US012275777B2

(12) United States Patent
Bilgischer et al.

(10) Patent No.: US 12,275,777 B2
(45) Date of Patent: *Apr. 15, 2025

(54) PROCESS FOR OBTAINING ANTIBODIES

(71) Applicant: UCB BIOPHARMA SRL, Brussels (BE)

(72) Inventors: Jean-Pascal Pierre Bilgischer, Brussels (BE); Philip Jonathan Bassett, Slough (GB); Mark Robert Pearce-Higgins, Slough (GB); Andrew John Kenny, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 101 days.

This patent is subject to a terminal disclaimer.

(21) Appl. No.: 17/858,112

(22) Filed: Jul. 6, 2022

(65) Prior Publication Data
US 2022/0348641 A1 Nov. 3, 2022

Related U.S. Application Data

(60) Division of application No. 16/674,003, filed on Nov. 5, 2019, now Pat. No. 11,384,136, which is a continuation of application No. 13/576,980, filed as application No. PCT/EP2011/051450 on Feb. 2, 2011, now Pat. No. 10,487,136.

(30) Foreign Application Priority Data

Feb. 3, 2010 (GB) ...................... 1001791

(51) Int. Cl.
*C07K 16/00* (2006.01)
*C12P 21/00* (2006.01)

(52) U.S. Cl.
CPC ............ *C07K 16/00* (2013.01); *C12P 21/00* (2013.01); *C07K 2317/14* (2013.01); *C07K 2317/55* (2013.01)

(58) Field of Classification Search
None
See application file for complete search history.

(56) References Cited

U.S. PATENT DOCUMENTS

| | | | |
|---|---|---|---|
| 5,665,866 A | 9/1997 | Weir et al. | |
| 6,083,715 A | 7/2000 | Georgiou et al. | |
| 7,012,135 B2 | 3/2006 | Athwal et al. | |
| 7,041,479 B2 | 5/2006 | Swartz et al. | |
| 8,470,552 B2 | 6/2013 | Croughan et al. | |
| 10,358,460 B2 | 7/2019 | Bassett et al. | |
| 10,487,136 B2 | 11/2019 | Bilgischer et al. | |
| 11,384,136 B2 | 7/2022 | Bilgischer et al. | |
| 2009/0252743 A1 | 10/2009 | Heavner et al. | |
| 2013/0178607 A1 | 7/2013 | Wild | |

FOREIGN PATENT DOCUMENTS

| WO | WO 01/94585 A1 * | 12/2001 | ............. C12N 15/13 |
|---|---|---|---|
| WO | WO 2006/054063 | 5/2006 | |
| WO | WO 2011/086138 | 7/2011 | |
| WO | WO 2011/086139 | 7/2011 | |
| WO | WO 2011/086141 | 7/2011 | |
| WO | WO 2012/013930 | 2/2012 | |

OTHER PUBLICATIONS

Bang et al. 'Anti-CD2 mAbs Suppress Cytotoxic Lymphocyte Activity by the Generation of Th2 Suppressor Cells and Receptor Blockade.' Biodrugs 18 (2):121-139, 2004.*
Valle et al. 'Infliximab' Expert Opin. Pharmacother. 2(6):1015-1025, 2001.*
Rice et al. Safety and efficacy of affinity-purified, anti-tumor necrosis factor-, ovine fab for injection (CytoFab) in severe sepsis* Crit Care Med 34(9):2271-2281, 2006.*
Chavin et al. Anti-CD2 mAbs Suppress Cytotoxic Lymphocyte Activity by the Generation of Th2 Suppressor Cells and Receptor Blockade J. Immunol. 152:3729-3738, 1994.*
Want, A. et al. "Studies Related to Antibody Fragment (Fab) Production in *Escherichia coli* W3110 Fed-Batch Fermentation Processes Using Multiparameter Flow Cytometry" *Cytometry Part A*, Feb. 2009, pp. 148-154, vol. 75, No. 2.
Hu, X. et al. "Optimisation of production of a domoic acid-binding scFv antibody fragment in *Escherichia coli* using molecular chaperones and functional immobilisation on a mesoporous silicate support" *Protein Expression and Purification*, 2007, pp. 192-201, vol. 52.
Hu, X. et al. "Cloning, Expression and Characterisation of a Single-Chain Fv Antibody Fragment Against Domoic Acid in *Escherichia coli*" *Journal of Biotechnology*, 2005, pp. 38-45, vol. 120.
Wunderlich, M. et al. "Bacterial Protein Disulfide Isomerase: Efficient Catalysis of Oxidative Protein Folding at Acidic pH" *Biochemistry*, 1993, pp. 12251-12256, vol. 32.
Liu, Z. et al., "The Influence of Coexpression of TrxA and DsbC to the Expression of Heterogenous Protein with Multiple Disulfide Bonds" *Chinese Journal of Biochemistry and Molecular Biology*, Aug. 30, 2002, pp. 486-489, vol. 18, No. 4.

* cited by examiner

*Primary Examiner* — Nora M Rooney
(74) *Attorney, Agent, or Firm* — SALIWANCHIK, LLOYD & EISENSCHENK

(57) ABSTRACT

The present disclosure relates to a method for the manufacture of recombinant antibody molecules comprising culturing a host cell sample transformed with an expression vector encoding a recombinant antibody molecule; adding an extraction buffer to the sample; and subjecting the sample to a heat treatment step; wherein the pH of the sample is detected after addition of the extraction buffer, and optionally adjusted, to ensure that the pH of the sample is 6 to 9 prior to the heat treatment step.

13 Claims, 11 Drawing Sheets

PROCESS FOR OBTAINING ANTIBODIES

CROSS-REFERENCE TO RELATED APPLICATIONS

This application is a divisional of U.S. application Ser. No. 16/674,003, filed Nov. 5, 2019, now U.S. Pat. No. 11,384,136, which is a continuation of U.S. application Ser. No. 13/576,980, filed Nov. 13, 2012, now U.S. Pat. No. 10,487,136, which is the U.S. national stage application of International Patent Application No. PCT/EP2011/051450, filed Feb. 2, 2011, the disclosures of which are hereby incorporated by reference in their entirety, including all figures, tables and amino acid or nucleic acid sequences.

This invention relates to methods for increasing the yields in the production and isolation of recombinant antibodies, and in particular therapeutic antibodies. The methods are particularly suitable for the large-scale industrial manufacture of therapeutic antibodies.

Recombinant DNA techniques have rapidly developed and are particularly useful in the production of antibodies, in particular therapeutic antibodies. Systems for the expression of recombinant genes are well known to the person skilled in the field in question. These include expression in mammalian cells, insect cells, fungal cells, bacterial cells and transgenic animals and plants. The choice of expression system is dependent on the features of the encoded protein, for example post-translational modifications. Other considerations include the time and, in particular, the cost involved in the production of the desired quantity of material of the required quality. These latter considerations are particularly important in the production of therapeutic antibodies of the quality required for regulatory approval and in the quantities needed for treatment of large numbers of patients.

The most widely used system for the production of recombinant proteins is based on expression in *Escherichia coli* (*E. coli*). A specific problem encountered with the use of *E. coli* is the difficulty in producing material of the required quality in quantities needed for therapy. In particular, the time and costs involved can be prohibitive. One specific problem of note is the loss incurred in the yield of antibodies during extraction of the antibodies from *E. coli*.

Although, proportionally, the purification costs are a fraction of the total cost of a therapeutic antibody product, the purification cost proportion will increase further as upstream production costs become cheaper. Thus, improvements in recovery and purification of antibodies will drive production costs down further irrespective of the means of production (Humphreys & Glover, Curr. Opin. Drug Discovery & Development, 2001, 4:172-185). Hence, there is a need for methods that introduce time and/or cost savings into therapeutic antibody production and, in particular, in purification, for example by increasing product recovery and/or improving the quality of the product stream.

Low product yield per fermentation or culture is often a particular problem noted at the primary extraction stage; expression of antibody is high within the cells but a high percentage recovery at the primary extraction stage is remarkably difficult to achieve.

A method that partially addresses this latter problem and that permits the production of antibodies acceptable for therapeutic use is described in U.S. Pat. No. 5,655,866. This method involves the use of heat treatment to facilitate the subsequent isolation of functional Fab' fragments of antibodies from non-functional antibodies, the heat treatment being performed at any time during the fermentation or culture, or at any stage during extraction and purification of the antibodies. At elevated temperatures, above room temperature, functional antibodies are remarkably stable, whilst many other proteins including host cell proteins and free light and heavy chain species and non-functional fragments of antibodies, form precipitates and/or aggregates which are easily separated from functional antibody during primary purification procedures such as filtration or centrifugation or fluidised bed chromatography. The cell extracts were prepared in the method described in U.S. Pat. No. 5,655,866 by incubating the intact cells in Tris HCl buffer 100 mM pH 7.4 containing EDTA 10 mM.

WO2006/054063 describes an increase in the yield of functional antibody at the primary extraction stage by the inclusion of a non-lysing treatment in combination with heat treatment. This method teaches that after centrifugation the cell pellets were resuspended in a sample comprising 1M Tris, pH 7.4 containing 100 mM EDTA followed by non-lysing treatment and then heat treatment.

WO2005/019466 describes an increase in yield of recombinant proteins by the inclusion of an interruption step under defined conditions of temperature and pH after fermentation but prior to downstream processing including extraction.

SUMMARY OF THE INVENTION

This invention described herein is based on the surprising and unexpected observation that after a host cell sample transformed with an expression vector encoding a recombinant antibody molecule has been cultured an increase in the pH of the resulting sample during the primary recovery process has a significant beneficial impact on the yield of antibody.

Whilst the antibody may start at a pH in the range 6-9 before processing, such as heating, surprisingly even when buffered the pH drops, probably as a result of cell metabolism. The present inventors now believe that this is detrimental to the yield/recovery and have proposed to address this by, where appropriate, adjusting the pH of the material before and/or during processing to ensure that the pH stays within the target range.

It has been surprisingly found that the pH of the sample prior to a heat treatment step has a considerable effect on the yield of antibody from the cell sample. It has been found that adjusting the pH of the sample such that the pH of the sample is pH 6 to 9 prior to the heat treatment step provides an increase in the yield of antibody of up to 40%. This enables hugely beneficial savings in time and cost of production of quantities of functional antibodies of therapeutic quality. Indeed other steps often used to increase yield, such as homogenization and hold steps, may no longer be required to achieve high levels of antibody yield.

In methods used previously, for example in U.S. Pat. No. 5,655,866, cell extracts were prepared by incubating the intact cells in a buffer having a pH of 7.4. It has been found that despite the addition of a buffer which would be expected to maintain the pH of the sample at a constant level, the pH of the cell sample in fact drops over time. In certain circumstances, such as over long periods of time following addition of a buffer, the pH of the sample has been found to be as low as pH 5.5 prior to the heat treatment step. It has been found that detecting and optionally adjusting the pH prior to heat treatment to ensure that the pH of the sample is 6 to 9 results in a surprising increase in the yield of antibody.

Whilst not wishing to be bound by theory, it is thought that it is important to maintain pH in the range 6 to 9 during the processing step, such as heat treatment. Adjusting the pH prior to processing (such as a heat treatment step) helps to maintain the pH in the right range. Therefore in one aspect there is provided an antibody extraction step wherein the pH is maintained substantially in the range 6 to 9, for substantially the duration of the process.

Without being bound by theory it is thought that the methods provided by the present invention allow the recovery of recombinant protein from the periplasm during primary isolation which is not released under standard extraction conditions.

Accordingly, in a first aspect of the present invention there is provided a method for the manufacture of recombinant antibody molecules comprising culturing a host cell sample transformed with an expression vector encoding a recombinant antibody molecule; adding an extraction buffer to the sample; and subjecting the sample to a heat treatment step; wherein the pH of the sample is detected after addition of the extraction buffer, and optionally adjusted, to ensure that the pH of the sample is 6 to 9 prior to the heat treatment step.

Monitoring of the pH at this stage is essential for establishing control over the pH.

In an alternative aspect there is provided a method for extraction of recombinant antibody molecules from a host cell sample transformed with an expression vector encoding a recombinant antibody molecule; comprising the steps of:

adjusting the pH of a composition of said cells to be in the range 6 to 9, such that the pH is maintained in the range during a subsequent extraction step, subjecting the cells to an extraction step, such as a heat treatment step, wherein the pH is monitored at least at one time point immediately before and/or during the extraction step.

It has also been found that an increase in the pH of the extraction buffer provides a surprising increase in the yield of antibody after the sample is subjected to a heat treatment step.

Accordingly, in a second aspect of the present invention there is provided a method for the manufacture of recombinant antibody molecules comprising culturing a host cell sample transformed with an expression vector encoding a recombinant antibody molecule; adding an extraction buffer to the sample having a pH of 7.5 to 9.0; and subjecting the sample to a heat treatment step.

DETAILED DESCRIPTION OF THE INVENTION

Antibody molecule as employed herein is intended to refer to a whole antibody or a binding fragment thereof, in particular a whole antibody or a Fab fragment.

In the first aspect of the present invention, the sample has or is adjusted to have a pH of 6 to 9 prior to the heat treatment step.

In a preferred embodiment the sample has a pH of 6.5 to 8.5, pH 6.5 to 8.0, pH 7.0 to 9.0, pH 7.0 to 8.5, pH 7.0 to 8.0, pH 7.1 to 8.0, pH 7.5 to 8.0, pH 7.0 to 7.8, pH 7.1 to 7.8, pH 7.1 to 7.7, pH 7.2 to 7.6, pH 7.3 to 7.5, pH 7.1, pH 7.2, pH 7.3, pH 7.4, pH 7.5, pH 7.6, pH 7.7, pH 7.8 or pH 7.9, such as pH 7.4, in particular pH 6.8 prior to the heat treatment step.

The pH measurement referred to herein is generally normalized to 20 degrees C.

The heat treatment step in the method of the present invention is a step of maintaining the temperature of the sample at a desired elevated temperature once this desired elevated temperature has been reached during a heat up phase. Suitable temperature ranges for the heat treatment step include 30 to 70° C.

In the context of the present invention the wording "prior to the heat treatment step" means before and including the point in time at which the sample reaches the desired elevated temperature and the heat treatment step (holding at an elevated temperature) commences. In order to reach the desired elevated temperature for the heat treatment step the sample is subjected to a "heat up phase" during which the temperature of the sample is elevated to the desired elevated temperature. In one embodiment the method according to the present invention comprises subjecting the sample to a heat up phase and a heat treatment step.

In the method of the present invention the sample has a pH of 6 to 9, for example pH 6.8 prior to the heat treatment step. In this context, "prior to the heat treatment step" means that the pH of the sample is at the required level before or at the point in time at which the sample reaches the desired elevated temperature for the heat treatment step. In the embodiment wherein the method comprises subjecting the sample to a heat up phase and a heat treatment step, the sample may be at the required pH level prior to the start of the heat up phase and/or at the required pH level during the heat up phase.

In a preferred embodiment, the sample is at the required pH level of 6 to 9 prior to the start of the heat up phase.

In one embodiment the present invention provides a method for the manufacture of recombinant antibody molecules comprising culturing a host cell sample transformed with an expression vector encoding a recombinant antibody molecule; adding an extraction buffer to the sample; and subjecting the sample to a heat up phase and a heat treatment step; wherein the pH of the sample is detected after addition of the extraction buffer, and optionally adjusted, to ensure that the pH of the sample is pH 6 to 9, for example pH 7 to 9, such as pH 7 to 8, prior to the heat up phase.

In an alternative embodiment the present invention provides a method for the manufacture of recombinant antibody molecules comprising culturing a host cell sample transformed with an expression vector encoding a recombinant antibody molecule; adding an extraction buffer to the sample; and subjecting the sample to a heat up phase and a heat treatment step; wherein the pH of the sample is detected after addition of the extraction buffer, and optionally adjusted, to ensure that the pH of the sample is pH 6 to 9, preferably pH 6 to 8, more preferably pH 6 to 7 during the heat up phase.

In the one embodiment the pH of the sample is detected and optionally adjusted to ensure that the pH of the sample is at a first pH prior to the heat up phase and at a second pH during the heat up phase. The first and second pH levels are preferably different. Preferably the second pH is lower than the first pH. Accordingly, the present invention provides a method for the manufacture of recombinant antibody molecules comprising culturing a host cell sample transformed with an expression vector encoding a recombinant antibody molecule; adding an extraction buffer to the sample; and subjecting the sample to a heat up phase and a heat treatment step; wherein the pH of the sample is detected after addition of the extraction buffer, and optionally adjusted, to ensure that the pH of the sample is pH 7 to 9, preferably pH 7 to 8, prior to the heat up phase and to ensure that the pH of the sample is pH 6 to 8, preferably pH 6 to 7 during the heat up phase. In this embodiment the pH of the sample may be detected and optionally adjusted prior to the heat up phase and detected and optionally adjusted during the heat up phase.

In a preferred embodiment the sample has a pH of 6 to 9, preferably pH 7 to 9, more preferably pH 7 to 8, immediately prior to the heat up phase. Additionally or alternatively, the sample has a pH of 6 to 9, preferably pH 6 to 8, more preferably pH 6 to 7 immediately prior to the heat treatment step during the heat up phase, optionally including the point at which the sample reaches the desired elevated temperature and the heat treatment step commences. It has been found that the pH of the sample immediately prior to the heat up phase or immediately prior to the heat treatment step has a significant impact on the yield of the recombinant antibody.

In the context of the present invention, the term "immediately prior to" preferably means for a period of 30 minutes or less, 20 minutes or less, 15 minutes or less, 10 minutes or less, 5 minutes or less, 4 minutes or less, 3 minutes or less, 2 minutes of less, 1 minute or less, 30 seconds or less, 10 seconds or less, 5 seconds or less, 1 second or less prior to the heat up phase the heat treatment step. The term "immediately prior to" may also encompass the pH of the solution being 6 to 9 at the start of the heat up phase or at the start of the heat treatment step.

The pH of the sample is detected after addition of the extraction buffer. The pH of the sample may be detected using any suitable pH measuring equipment known in the art. The pH of the sample may be detected at one or more separate points during the method, such as at the point of adding the extraction buffer, immediately after adding the extraction buffer, immediately before starting the heat up phase, at the point of starting the heat up phase, during the heat up phase including the point at which the sample reaches the desired elevated temperature for the heat treatment step, during the heat treatment step and after the heat treatment step. Alternatively, the pH of the sample is detected by continuous monitoring. In this embodiment wherein the pH of the sample is continuously monitored, the pH is preferably continuously monitored from after the step of culturing the cells, preferably after a step of centrifugation following culturing, to the start of the heat treatment step. In a preferred embodiment the pH of the sample is monitored continuously from the point of adding the extraction buffer to the start of the heat treatment step. However, the pH may also be monitored during the culture step and/or during the heat treatment step.

Thus in one embodiment the pH profile of the heating step is controlled.

In a preferred embodiment the pH of the sample is detected, and optionally adjusted, and the heat up phase is started, preferably automatically, when the sample reaches the desired pH.

The extraction buffer is added after the step of culturing the cell sample. If the method comprises a step of centrifugation after the step of culturing, the extraction buffer may be added before and/or during and/or after the step of centrifugation. Preferably the extraction buffer is added after a step of centrifugation to re-suspend the resulting cell pellet from the centrifugation.

In one embodiment of the present invention the extraction buffer has a suitable pH which ensures that the pH of the sample is pH 6 to 9, for example pH 6 to 8, prior to the heat treatment step. In this embodiment where the extraction buffer has a suitable pH to ensure that the pH of the sample is 6 to 9, for example pH 6 to 8, prior to heat treatment, the extraction buffer for example has a pH of pH 7.5 to 9.0, pH 7.5 to 8.8, pH 7.5 to 8.5, pH 8.0 to 9.0, pH 8.5 to 9.0, pH 8.6 to 8.9, pH 8.0, pH 8.1, pH 8.2, pH 8.3, pH 8.4, pH 8.5, pH 8.6, pH 8.7, pH 8.8, pH, 8.9 or pH 9.0. The heat-up phase and heat treatment step are preferably carried out soon after, preferably immediately after, addition of the extraction buffer in order to ensure that the sample has the required pH prior to the heat treatment step. For example, the heat-up phase or the heat treatment step may be carried out 4 hours of less, 3 hours or less, 2 hours or less, 1 hour or less, 30 minutes or less, 10 minutes or less or 5 minutes or less after addition of the extraction buffer.

Accordingly, the method of the present invention may not require a step of pH adjustment of the sample. The pH of the sample may be detected after addition of the extraction buffer to be pH 6 to 9 as required. This may for example be the case if the pH of the extraction buffer is suitable to bring the pH of the sample to 6 to 9 as described above e.g. wherein the extraction buffer has a pH of 7.5 to 9.0 and the heat treatment step is carried out shortly afterwards.

Typically, however, due to the length of time between the addition of the extraction buffer and the heat treatment step, the method according to the present invention requires a step of detecting and adjusting the pH of the sample, in addition to any pH adjustment which may be caused by adding the extraction buffer, to ensure that the pH of the sample is 6 to 9 prior to the heat treatment step.

In this embodiment wherein the method comprises a step of pH detection and adjustment, the pH of the extraction buffer may be less than pH 8, such as pH 7.4 or less, for example pH 6.0 to 7.4, pH 6.5 to 7.4 or pH 7.0 to 7.4, such as pH 6.8.

Alternatively, in a preferred embodiment the extraction buffer has a pH of 7.5 to 9.0, pH 7.5 to 8.8, pH 7.5 to 8.5, pH 8.0 to 9.0, pH 8.5 to 9.0, pH 8.6 to 8.9, pH 8.0, pH 8.1, pH 8.2, pH 8.3, pH 8.4, pH 8.5, pH 8.6, pH 8.7, pH 8.8, pH, 8.9, pH 9.0 most preferably pH 8.0.

In this embodiment, the pH of the sample may be adjusted by any suitable means and at any suitable time during the method. The pH of the sample may be adjusted prior to and/or after addition of the extraction buffer.

In one embodiment the pH of the sample is adjusted prior to the addition of the extraction buffer. In this embodiment if the method comprises a step of centrifugation following the step of culturing, the step of pH adjustment may be carried out before and/or after the step of centrifugation. The pH of the sample after culturing the cells, and optionally after centrifugation, is typically low. For example, the sample may have a pH of around pH 5.5. Accordingly, after culturing the cells and optionally after one or more additional steps, such as centrifugation, the pH of the sample may be adjusted. For example the pH of the sample may be adjusted prior to addition of the extraction buffer to pH 6.5 to 8.0, preferably pH 7.0 to 8.0, pH 6.5 to 7.5, pH 6.6 to 7.4, pH 6.7 to 7.3, pH 6.8 to 7.2, pH 6.9 to 7.1, most preferably pH 6.9.

In one embodiment wherein the pH of the sample prior to addition of the extraction buffer is less than pH 7, such as pH 6.9, and the pH of the sample prior to the heat treatment step is required to be pH 7 to 9, the pH of the sample requires further elevation by the addition of the extraction buffer and/or by further pH adjustment after addition of the extraction buffer such that the pH of the sample is 7 to 9 prior to the heat treatment step.

In a preferred embodiment of the present invention the pH of the sample is adjusted to pH 6 to 9 after addition of the extraction buffer but prior to the heat treatment step. At this stage the sample is preferably adjusted to pH 7.0 to 9.0, pH 7.0 to 8.5, pH 7.0 to 8.0, pH 7.1 to 8.0, pH 7.5 to 8.0, pH 7.0 to 7.8, pH 7.1 to 7.8, pH 7.1 to 7.7, pH 7.2 to 7.6, pH 7.3 to 7.5, pH 7.1, 7.2, 7.3, 7.4, 7.5, 7.6, 7.7, 7.8 or 7.9 and most preferably pH 7.4. In one embodiment the pH of the sample is adjusted prior to the heat up phase. Preferably, the pH of the sample is adjusted to pH 7 to 9, preferably pH 7 to 8, prior to the heat up phase. Alternatively or additionally, the pH of the sample is adjusted during the heat up phase. Preferably, the pH of the sample is adjusted to pH 6 to 8, preferably pH 6 to 7 during the heat up phase.

In a preferred embodiment of the present invention an extraction buffer having a pH of 7.4 or pH 8 is added to the sample and the pH of the sample is detected and subsequently adjusted to a pH of 7.4 prior to the heat treatment step, preferably prior to the heat up phase, more preferably immediately prior to the heat up phase.

In the embodiment wherein the pH of the sample is detected after addition of the extraction buffer and adjusted prior to the heat treatment step, the pH of the sample may be detected and adjusted prior to the start of the heat up phase. Additionally or alternatively the pH of the sample may be detected and adjusted during the heat up phase.

In a preferred embodiment the pH of the sample is detected and adjusted immediately prior to the heat up phase. Additionally or alternatively, the pH of the sample is detected and adjusted immediately prior to the heat treatment step during the heat up phase, optionally including the point at which the sample reached the desired elevated temperature and the heat treatment step commences.

In the context of the present invention, the term "immediately prior to" preferably means that the pH of the sample is detected and adjusted to pH 6 to 9 for 30 minutes or less, 20 minutes or less, 15 minutes or less, 10 minutes or less, 5 minutes or less, 4 minutes or less, 3 minutes or less, 2 minutes of less, 1 minute or less, 30 seconds or less, 10 seconds or less, 5 seconds or less, 1 second or less prior to the heat up phase or prior to the heat treatment step. The term "immediately prior to" may also encompass the pH of the solution being detected and adjusted at the start of the heat up phase or at the start of the heat treatment step. In a preferred embodiment, heat up phase and/or heat treatment step is triggered, preferably automatically when the pH of the sample is detected to be pH 6 to 9.

The pH of the sample may be detected and adjusted by any single or multiple steps of pH adjustment as described above. Accordingly, the pH may be adjusted:
  only prior to addition of the extraction buffer;
  only after addition of the extraction buffer but prior to the heat treatment step; or
  prior to addition of the extraction buffer and after addition of the extraction buffer but prior to the heat treatment step.

The pH may be adjusted multiple times after the addition of extraction buffer, for example 1, 2, 3, 4 or more times.

In one embodiment the pH of the sample is continuously adjusted, preferably between the addition of the extraction buffer and prior to the heat treatment step.

The pH of the sample may in one embodiment be additionally detected and optionally adjusted during the heat treatment step. Accordingly, the method according to the present invention may further include a step of adjusting the pH of the sample during the heat treatment step. The pH of the sample is preferably adjusted during the heat treatment step to pH 6.0 to 9.0, pH 6.5 to 8.5, pH 6.5 to 8.0, pH 7.0 to 9.0, pH 7.0 to 8.5, pH 7.0 to 8.0, pH 7.1 to 8.0, pH 7.5 to 8.0, pH 7.0 to 7.8, pH 7.1 to 7.8, pH 7.1 to 7.7, pH 7.2 to 7.6, pH 7.3 to 7.5, pH 7.1, 7.2, 7.3, 7.4, 7.5, 7.6, 7.7, 7.8 or 7.9.

In the second aspect according to the present invention there is provided a method for the manufacture of recombinant antibody molecules comprising culturing a host cell sample transformed with an expression vector encoding a recombinant antibody molecule; adding an extraction buffer to the sample having a pH of 7.5 to 9.0; and subjecting the sample to a heat treatment step.

As described above in the first aspect of the present invention, the extraction buffer preferably has a pH of 7.5 to 9.0, pH 7.5 to 8.8, pH 7.5 to 8.5, pH 8.0 to 9.0, pH 8.5 to 9.0, pH 8.6 to 8.9, pH 8.0, pH 8.1, pH 8.2, pH 8.3, pH 8.4, pH 8.5, pH 8.6, pH 8.7, pH 8.8, pH, 8.9 or pH 9.0. In this aspect of the present invention it is not essential to detect the pH of the sample. The method according to the second aspect of the present invention may comprise detecting the pH of the sample and adjusting the pH of the sample as described in the first aspect of the present invention. However, it is not essential to include a step of detecting pH or adjusting pH. In one embodiment the method according to the second aspect of the invention does not include a step of detecting the pH of the sample or a step of pH adjustment.

The following detailed description of the invention applies to embodiments of both the first and second aspects of the present invention.

pH Adjustment Agent and Extraction Buffer

The pH adjustment must be such that the pH is sustained/maintained in the desired range of pH 6-9 during the heat treatment step.

In one embodiment the pH is adjusted with a base such as an inorganic base for example sodium hydroxide or an organic base such as triethylamine or trimethylamine.

Any suitable agent may be used to adjust the pH of the sample. The agent may be the extraction buffer or may be added before and/or after the extraction buffer. Typical agents which may be used to adjust the pH comprises or consists of one or more of the following: NaOH, NH$_4$OH, Sulphuric acid, EDTA, Tris buffer. Preferably the pH of the sample is adjusted using a base such as sodium hydroxide or ammonium hydroxide.

In one embodiment the extraction buffer is a Tris(hydroxymethyl)aminomethan/Ethylenedinitrilotetraacetic acid disodium salt dehydrate (Tris/EDTA) buffer typically adjusted to a desired pH by addition of HCl. Without being bound by theory it is thought that Tris and EDTA work synergistically in releasing lipopolysaccarides (LPS) from the outer membrane of E. coli. EDTA removes divalent cations that stabilize LPS of the outer membrane. It is thought that Tris binds to LPS and replaces Ca$^{2+}$ and Mg$^{2+}$. This results in a reduction of interactions between LPS molecules and therefore increased permeability of the outer membrane (Vaara, M. 1992. Agents That Increase the Permeability of the Outer Membrane. American Society for Microbiology 56:395-411).

Heat Treatment Step

The heat treatment step in the method of the present invention is preferably as described in detail in U.S. Pat. No. 5,665,866 (the contents of which are incorporated herein by reference). The heat treatment step makes it possible to obtain a sample of soluble, correctly folded and assembled antibody by facilitating the removal of other antibody-related material. Antibody which is "correctly folded and assembled" is shown by the presence of a single band corresponding to the expected molecular weight for assembled heavy and light chains on non-reducing SDS PAGE. Other antibody related material will typically be free heavy and light chain or part thereof, partially degraded fragments of correctly folded and assembled antibody.

The heat treatment step is performed by subjecting the sample to a desired elevated temperature. Most preferably, heat treatment step is performed within the range of 30° C. to 70° C. The temperature can be selected as desired and may depend on the stability of the antibody for purification. In another embodiment, the temperature is within the range 40° C. to 65° C., or preferably within the range 40° C. to 60° C., more preferably within the range 45° C. to 60° C., even more preferably within the range 50° C. to 60° C. and most preferably at 55° C. to 60° C., 58° C. to 60° C. or 59° C. Thus, the minimum temperatures are 30° C., 35° C. or 40° C. and the maximum temperatures 60° C., 65° C. or 70° C.

The heat treatment step is preferably carried out for a prolonged period of time. The length of heat treatment is preferably between 1 and 24 hours, more preferably between 4 and 18 hours, even more preferably between 6 and 16 hours and most preferably between 10 and 14 hours or between 10 and 12 hours, for example 12 hours. Thus, the minimum time for heat treatment is 1, 2 or 3 hours and the maximum is 20, 22 or 24 hours.

In a particular embodiment, the heat treatment is performed at 50° C. to 60° C. for 10 to 16 hours, and more preferably at 59° C. for 10 to 12 hours. One skilled in the art will understand that temperatures and time can be selected as suits the sample in question and the characteristics of the antibody being produced.

In one embodiment the process according to the present disclosure does not include a pre-treatment step of holding the cells under controlled conditions prior to performing the heat treatment step.

In a preferred embodiment, the present invention provides a method for the manufacture of recombinant antibody molecules comprising culturing a host cell sample transformed with an expression vector encoding a recombinant antibody molecule and adding an extraction buffer to the sample and subjecting the sample to a heat treatment step within the range of 40° C. to 70° C., preferably 59° C., for a period of up to 15 hours, preferably 10-12 hours, wherein prior to the heat treatment step the pH of the sample is monitored and adjusted such that the pH of the sample is pH 7 to 8, preferably pH 7.4, prior to the heat treatment step, preferably immediately prior to the heat up phase. Preferably an extraction buffer having a pH of 7.4 or 8.0 is added to the sample.

The heat treatment step is preferably carried out in a shaker set at a suitable RPM, such as 200 RPM. However, the suitable RPM will vary depending upon the scale of the method.

Fermentation

The step of culturing a host cell sample may comprise fermentation at any desired scale. In the methods of the invention a sample may be the product of a fermentation comprising bacteria, especially gram-negative bacteria, or yeast, a cell culture, for example but without limitation, a mammalian or insect cell culture. Most preferably, the sample is the product of a fermentation comprising *E. coli* expressing a recombinant antibody, wherein said antibodies produced may be a mixture of functional and non-functional antibodies. If desired, the host cells may be subject to collection from the fermentation medium, e.g. host cells may be collected from the sample by centrifugation, filtration or by concentration. In particular, the methods of the invention are suitable for the large-scale industrial manufacture of antibodies of therapeutic quality.

Further Steps

The method according to the present invention may comprise one or more further steps.

In one embodiment the method according to the present invention comprises a step of centrifugation after the step of culturing, followed by suspension of the cells by addition of the extraction buffer.

The method may additionally comprise primary purification procedures such as filtration and/or centrifugation. Also included is fluidised bed chromatography. Preferred downstream purification procedures include ion exchange chromatography, microfiltration, ultrafiltration, diafiltration, and fixed bed capture and expanded bed capture, and combinations of any of these.

Non-Lysis Treatment Step

The method may further comprise subjecting the sample to a non-lysing treatment step before subjecting the sample to the heat treatment step. This step may also be referred to as a homogenization step (homog. step). The non-lysing treatment step may further increase yield of functional antibodies isolated or obtained and ease of handling of the sample on a large scale. Lysis causes an increase in viscosity which can cause problems in downstream processing and purification of functional antibody. In particular, lysis of host cells causes release of host cell proteins making purification more expensive and time consuming as more purification steps may be required and/or larger quantities of chromatography materials will be needed to achieve the required purity. Substantial release of host cell DNA increases sample viscosity causing filtration and centrifugation difficulties which is a major cause of protein loss during clarification. A lysed sample (i.e., containing host cell proteins and DNA) can also cause blockage of chromatographic materials. The non-lysing treatment step is preferably carried out as described in WO 2006/054063 (the contents of which are incorporated herein by reference). As described in WO 2006/054063, the non-lysing treatment step includes any treatment which does not produce lysis of a substantial proportion of the bacteria, mammalian cell, yeast, insect cell, or other organism used for recombinant antibody expression, e.g. *E. coli*. In a most preferred embodiment, the non-lysing treatment comprises pressure treatment. Alternatively, the non-lysing treatment comprises a pre-conditioning step of agitation or stirring. A "substantial proportion" includes a proportion of 80% or more of the organisms in a fermentation or culture being present in intact form, more preferably more than 85%, even more preferably more than 90%, and most preferably 95% or more being intact.

Lysis can be judged in any way known in the art, including: by viewing under a microscope, fluorescence activated cell sorting (FACS) analysis and assay of total protein versus protein in supernatant and/or in an organism (cell) pellet. In one embodiment, lysis can be judged after non-lysing treatment by comparing the total protein in a sample before and after treatment. If a treatment is causing lysis, the total protein present in the supernatant of the treated sample would increase compared to the total protein present in said untreated sample, for example measured using a Bradford assay. In a preferred embodiment, FACS analysis is performed wherein the sample is labelled with a fluorescent dye followed by non-lysing treatment and FACS analysis. Most preferably, FACS analysis is performed before treatment giving a baseline value for comparison.

Thus, non-lysing treatment can include pre-conditioning by gentle resuspension over a period of time, for example by agitation or stirring, or by manual resuspension such as by pipetting, in, e.g. a buffer. In one embodiment, pre-conditioning is performed for between 1 hour and 24 hours, preferably between 1 hour and 20 hours, more preferably between 2 hours and 18 hours, 4 hours and 16 hours, 6 hours and 16 hours, and most preferably for 12, 14 or 16 hours. Thus, the minimum time for pre-conditioning is 1, 2 or 4 hours and the maximum is 16, 18 or 24 hours. Pre-conditioning can be performed by rotation at 50 to 250 rpm, preferably at 60 rpm to 100 rpm, and most preferably for 14 or 16 hours. During pre-conditioning the cells are maintained at a temperature within the range of 4° C. to 30° C., more preferably between 4° C. to 20° C. and most preferably at room temperature.

In one embodiment the pre-conditioning step does not comprise part of the process.

In a preferred embodiment, non-lysing treatment comprises subjecting the host cells to increased pressures, for example using a French press or nitrogen decompression.

In a specific example, the sample is the product of an *E. coli* fermentation, said *E. coli* expressing a recombinant antibody, which is subjected to pressure treatment in a French press. Pressures may range from 750 psi or thereabouts to 5000 psi or thereabouts. In one embodiment, the pressure treatment is performed at 1000 psi, or 1250 psi, 1500 psi, 1750 psi, 2000 psi, 2250 psi, 2500 psi, 2750 psi, 3000 psi, 3250 psi, 3500 psi, 4000 psi, 4250 psi, 4500 psi or 4750 psi. More preferably, the pressure treatment is performed at between 1000 psi and 3000 psi, and most preferably at 2000 psi. Pressure treatment which is substantially non-lysing (i.e. causing less than 20% lysis) may be determined by simple experimentation depending on the buffer and cell type comprising the sample, and the pressure.

In one embodiment of the present invention the method does not include a non-lysing treatment step as described above, such as subjecting the host cells to increased pressures or pre-conditioning by gentle resuspension over a period of time. The inclusion of such a non-lysing treatment step is known to improve the yield of a recombinant protein (WO 2006/054063). However, it has been surprisingly found that the improved yield of antibody is achieved by the method of the present invention with or without such a non-lysing treatment step. Accordingly, the embodiment wherein the method does not comprise a non-lysing treatment step the present invention provides a more simplified and cost-effective means for providing a recombinant antibody.

Hold Step

In one embodiment the method according to the present invention comprises a step of interrupting the method between the step of culturing the host cell sample and prior to addition of the extraction buffer. During the interruption step the samples is maintained at a suitable temperature. This step of interrupting the method is preferably carried out as described in WO 2005/019466. This step may also be referred to as a cell slurry hold step (CSH). Preferably the method is interrupted for a period of at least about one hour, 1 hour to 72 hours, 12 hours to 48 hours, for 12 hours, 24 hours, 33 hours or 48 hours.

The sample is preferably held at a suitable temperature during the interruption of the method, such as 18° C.

In one embodiment of the present invention the method does not include an interruption step after the step of culturing the host cell sample, such as described in WO 2005/019466. The inclusion of such an interruption is known to improve the yield of a recombinant protein (WO 2005/019466). It has been surprisingly found that a similar improvement in yield of antibody is achieved by the method of the present invention with or without such an interruption step i.e. no further increase in yield was observed when the interruption step was included in the method. Accordingly, the embodiment wherein the method does not comprise an interruption step the present invention provides a more simplified and cost-effective means for providing a recombinant antibody. Accordingly, in one embodiment the time period between the step of culturing the host cell sample and the step of adding the extraction buffer is less than 12 hours, preferably 10 hours or less, 5 hours or less, 4 hours or less, 3 hours or less, 2 hours or less or 1 hour or less or less than 1 hour.

Antibody

As used herein, 'functional antibody' includes antibody molecules that retain the ability to specifically recognise or bind to the antigen against which they were raised (cognate antigen). The production of a functional antibody is shown by the presence of a single band on non-reducing SDS-PAGE corresponding to the expected molecular weight of the antibody, or by direct binding assay using BIAcore or other methods known to the person skilled in the art, for example but not limited to, ELISA. Non-functional antibodies include fragments which do not recognise their cognate antigen, and include incorrectly-folded or incorrectly-assembled antibodies, free heavy and light chains, and fragments thereof, including partially degraded fragments of antibodies which do not recognise or bind to their cognate antigen.

In a preferred example, the recombinant antibody molecule is at least part of an antibody light chain and at least part of an antibody heavy chain, such that at least some of the expressed light and heavy chain antibody molecules are able to combine to form functional antibody.

As used herein, 'antibodies' include antibodies having full length heavy and light chains; functionally active fragments, derivatives or analogues thereof and may be, but are not limited to VH, VL, VHH, Fab, modified Fab, an altered hinge Fab, Fab', F(ab')$_2$ or Fv fragment; a light chain or heavy chain monomer or dimer; a single chain antibody, e.g. a single chain Fv in which the heavy and light chain variable domains are joined by a peptide linker, or a dual specificity antibody, such as a Fab-dAb, as described in PCT/GB2008/003331.

The antibodies may be polyclonal, monoclonal, bi-, tri- or tetra-valent antibodies, humanized or chimeric antibodies. These antibodies and their fragments may be naturally occurring, humanized, chimeric or CDR grafted antibodies and standard molecular biology techniques may be used to modify, add or delete amino acids or domains as desired. Humanized antibodies are antibody molecules from non-human species having one or more complementarity determining regions (CDRs) from the non-human species and a framework region from a human immunoglobulin molecule (see, for example, U.S. Pat. No. 5,585,089). The antibody molecules purified using the methods of the invention can be of any class (e.g. IgG, IgE, IgM, IgD and IgA) or subclass of immunoglobulin molecule.

The methods for creating these antibody molecules are well known in the art (see for example, Shrader et al., WO 92/02551; Ward et al., 1989, Nature, 341:544; Orlandi et al., 1989, Proc. Natl. Acad. Sci. USA, 86:3833; Riechmann et al., 1988, Nature, 322:323; Bird et al, 1988, Science, 242: 423; Queen et al., U.S. Pat. No. 5,585,089; Adair, WO91/09967; Mountain and Adair, 1992, Biotechnol. Genet. Eng. Rev, 10:1-142; Verma et al., 1998, Journal of Immunological Methods, 216:165-181).

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Chimeric antibodies are those antibodies encoded by immunoglobulin genes that have been genetically engineered so that the light and heavy chain genes are composed of immunoglobulin gene segments belonging to different species. These chimeric antibodies are likely to be less antigenic. Bivalent antibodies may be made by methods known in the art (Milstein et al., 1983, Nature 305:537-539; WO 93/08829, Traunecker et al., 1991, EMBO J. 10:3655-3659). Bi-, tri- and tetra-valent antibodies may comprise multiple specificities or may be monospecific (see for example WO 92/22853).

Antibody sequences may also be generated using single lymphocyte antibody methods based on the molecular cloning and expression of immunoglobulin variable region cDNAs generated from single lymphocytes that were selected for the production of specific antibodies such as described by Babcook, J. et al., 1996, Proc. Natl. Acad. Sci. USA 93(15):7843-7848 and in WO 92/02551. The latter methods rely on the isolation of individual antibody producing cells which are then clonally expanded followed by screening for those clones which are producing an antibody which recognises its cognate antigen, and, if desired, the subsequent identification of the sequence of their variable heavy ($V_H$) and light ($V_L$) chain genes. Alternatively, the cells producing antibody that recognises its cognate antigen may be cultured together followed by screening.

Antibodies prepared using the methods of the invention are most preferably humanised antibodies which may be subsequently linked to toxins, drugs, cytotoxic compounds, or polymers or other compounds which prolong the half-life of the antibody when administered to a patient.

The antibody may be specific for any target antigen. The antigen may be a cell-associated protein, for example a cell surface protein on cells such as bacterial cells, yeast cells, T-cells, endothelial cells or tumour cells, or it may be a soluble protein. Antigens of interest may also be any medically relevant protein such as those proteins upregulated during disease or infection, for example receptors and/or their corresponding ligands. Particular examples of cell surface proteins include adhesion molecules, for example integrins such as β1 integrins e.g. VLA-4, E-selectin, P selectin or L-selectin, CD2, CD3, CD4, CD5, CD7, CD8, CD11a, CD11b, CD18, CD19, CD20, CD23, CD25, CD33, CD38, 40, CD40L, CD45, CDW52, CD69, CD134 (OX40), ICOS, BCMP7, CD137, CD27L, CDCP1, CSF1 or CSF1-Receptor, DPCR1, DPCR1, dudulin2, FLJ20584, FLJ40787, HEK2, KIAA0634, KIAA0659, KIAA1246, KIAA1455, LTBP2, LTK, MAL2, MRP2, nectin-like2, NKCC1, PTK7, RAIG1, TCAM1, SC6, BCMP101, BCMP84, BCMP11, DTD, carcinoembryonic antigen (CEA), human milk fat globulin (HMFG1 and 2), MHC Class I and MHC Class II antigens, KDR and VEGF, and where appropriate, receptors thereof.

Soluble antigens include interleukins such as IL-1, IL-2, IL-3, IL-4, IL-5, IL-6, IL-8, IL-12, IL-13, IL-14, IL-16 or IL-17, such as IL17A and/or IL17F, viral antigens for example respiratory syncytial virus or cytomegalovirus antigens, immunoglobulins, such as IgE, interferons such as interferon α, interferon β or interferon γ, tumour necrosis factor TNF (formerly known as tumour necrosis factor-α), tumor necrosis factor-β, colony stimulating factors such as G-CSF or GM-CSF, and platelet derived growth factors such as PDGF-α, and PDGF-β and where appropriate receptors thereof. Other antigens include bacterial cell surface antigens, bacterial toxins, viruses such as influenza, EBV, HepA, B and C, bioterrorism agents, radionuclides and heavy metals, and snake and spider venoms and toxins.

In one embodiment, the antibody may be used to functionally alter the activity of the antigen of interest. For example, the antibody may neutralize, antagonize or agonise the activity of said antigen, directly or indirectly.

In a preferred embodiment the antibody is an anti-TNF antibody, more preferably an anti-TNF Fab', as described in WO01/094585 (the contents of which are incorporated herein by reference).

Methods for the expression of recombinant proteins are well known in the art. Suitable examples of host cells for the expression of recombinant antibody molecules include bacteria such as gram positive or gram negative bacteria, e.g. *E. coli*, or yeast cells, e.g. *S. cerevisiae*, or mammalian cells, e.g. CHO cells and myeloma or hybridoma cell lines, e.g. NSO cells. Most preferably, in the methods of the invention, a recombinant antibody is produced in bacteria, e.g. *E. coli* (see Verma et al., 1988, J. Immunol. Methods 216:165-181; Simmons et al., 2002, J. Immunol. Methods 263:133-147).

Cells

The term "sample" used in the present invention refers to a population of cells which have been transformed with an expression vector encoding a recombinant antibody molecule. The sample may be at any suitable scale from small-scale production of antibody to large-scale manufacture of antibody for commercial purposes.

The cells used in the present invention may be for example but without limitation bacteria, especially gram-negative bacteria, yeast, mammalian or insect. Most preferably, the cells are *E. coli*. The cells may be wild-type cells or recombinant cells which have been genetically engineered. *E. coli* host cells may be naturally occurring *E. coli* strains or mutated strains capable of producing recombinant proteins. Examples of specific host *E. coli* strains include MC4100, TG1, TG2, DHB4, DH5α, DH1, BL21, K12, XL1Blue and JM109. One example is *E. coli* W3110 (ATCC 27,325) a commonly used host strain for recombinant protein fermentations. Examples also include modified *E. coli* strains, for example metabolic mutants and protease deficient strains.

The recombinant antibody produced using the methods of the present invention is typically expressed in either the periplasm of the *E. coli* host cell or in the host cell culture supernatant, depending on the nature of the protein and the scale of production. The methods for targeting proteins to these compartments are well known in the art, for a review see Makrides, Microbiological Reviews, 1996, 60, 512-538. Examples of suitable signal sequences to direct proteins to the periplasm of *E. coli* include the *E. coli* PhoA, OmpA, OmpT, LamB and OmpF signal sequences. Proteins may be targeted to the supernatant by relying on the natural secretory pathways or by the induction of limited leakage of the outer membrane to cause protein secretion examples of which are the use of the pelB leader, the protein A leader, the coexpression of bacteriocin release protein, the mitomycin-induced bacteriocin release protein along with the addition of glycine to the culture medium and the coexpression of the kil gene for membrane permeabilization. Most preferably, in the methods of the invention, the recombinant protein is expressed in the periplasm of the host *E. coli*.

Expression of the recombinant protein in the *E. coli* host cells may also be under the control of an inducible system, whereby the expression of the recombinant antibody in *E. coli* is under the control of an inducible promoter. Many inducible promoters suitable for use in *E. coli* are well known in the art and depending on the promoter, expression of the recombinant protein can be induced by varying factors such as temperature or the concentration of a particular substance in the growth medium (Baneyx, Current Opinion in Biotechnology, 1999, 10:411-421; Goldstein and Doi, 1995, Biotechnol. Annu. Rev, 105-128). Examples of inducible promoters include the *E. coli* lac, tac, and trc promoters which are inducible with lactose or the non-hydrolyzable lactose analog, isopropyl-β-D-1-thiogalactopyranoside (IPTG) and the phoA, trp and araBAD promoters which are induced by phosphate, tryptophan and L-arabinose respectively. Expression may be induced by, for example, the addition of an inducer or a change in temperature where induction is temperature dependent. Where induction of recombinant protein expression is achieved by the addition of an inducer to the culture the inducer may be added by any suitable method depending on the fermentation system and the inducer, for example, by single or multiple shot additions or by a gradual addition of inducer through a feed. It will be appreciated that there may be a delay between the addition of the inducer and the actual induction of protein expression for example where the inducer is lactose there may be a delay before induction of protein expression occurs while any pre-existing carbon source is utilized before lactose.

*E. coli* host cell cultures (fermentations) may be cultured in any medium that will support the growth of *E. coli* and expression of the recombinant protein. The medium may be any chemically defined medium, such as those provided in Pirt S. J. (1975) Principles of Microbe and Cell Cultivation, Blackwell Scientific Publications, with modifications where appropriate to control growth rate as described herein. An example of a suitable medium is 'SM6E' as described by Humphreys et al., 2002, Protein Expression and Purification, 26:309-320.

Culturing of the *E. coli* host cells can take place in any suitable container such as a shake flask or a fermenter depending on the scale of production required. Various large scale fermenters are available with a capacity of more than 1,000 litres up to about 100,000 litres. Preferably, fermenters of 1,000 to 50,000 litres are used, more preferably 1,000 to 10,000 or 12,000 litres. Smaller scale fermenters may also be used with a capacity of between 0.5 and 1,000 litres.

Fermentation of *E. coli* may be performed in any suitable system, for example continuous, batch or fed-batch mode (Thiry & Cingolani, 2002, Trends in Biotechnology, 20:103-105) depending on the protein and the yields required. Batch mode may be used with shot additions of nutrients or inducers where required. Alternatively, a fed-batch culture may be used and the cultures grown in batch mode pre-induction at the maximum specific growth rate that can be sustained using the nutrients initially present in the fermenter and one or more nutrient feed regimes used to control the growth rate until fermentation is complete. Fed-batch mode may also be used pre-induction to control the metabolism of the *E. coli* host cells and to allow higher cell densities to be reached (Lee, 1996, Tibtech, 14:98-105).

Preferred features of each embodiment of the invention are as for each of the other embodiments mutatis mutandis. All publications, including but not limited to patents and patent applications cited in this specification are herein incorporated by reference as if each individual publication were specifically and individually indicated to be incorporated by reference herein as though fully set forth.

In one aspect there is provided an antibody obtained or obtainable from said process.

In one aspect there is provide use of pH controlling means, such as a buffer, to improve antibody extraction, for example primary extraction, in particular where the control ensures the pH is maintained in the range pH 6 to 9 during an extraction step, such as a heat extraction step.

pH controlling means as employed herein is buffer, base and/or acid.

The invention will now be described with reference to the following examples, which are merely illustrative and should not in any way be construed as limiting the scope of the present invention.

FIG. 1 is a graph showing the pH of cells resuspended in Tris/EDTA extraction buffer of pH 7.4 and pH 8 over time.

FIG. 2*a* is a histogram showing the effect of the pH of the extraction buffer on the yield of antibody A.

FIG. 2*b* is a histogram showing the pH of cell samples (resuspended cell slurry) directly after addition of an extraction buffer having a pH from 7.4 to 9.0 and the pH of the cell samples 1 hour after addition of the extraction buffer prior to the heat up phase.

FIG. 3*a* is a histogram showing the effect of adjusting the pH of the sample prior to the heat treatment step on the yield of antibody A. Numbers above each bar indicate the % increase in yield compared to the control with no step of pH adjustment.

FIG. 3*b* is a graph showing the varying pH of the samples through the various stages of the method: the cell slurry (after culturing and centrifugation); post buffer addition (directly after addition of the extraction buffer); pre pH adjustment; post pH adjustment but pre heat up phase; and post heat treatment step.

FIG. 4 shows an SDS-PAGE analysis of antibody A samples extracted from cells after heat treatment. Lane 1 is a molecular weight marker, Lane 2 is a sample of antibody A, Lane 3 is the sample after no pH adjustment and Lanes 4 to 8 show samples after pH adjustment to 7.0, 7.2, 7.4, 7.6 and 7.8 respectively prior to the heat treatment step.

FIG. 5 is a histogram showing the effect of using an extraction buffer at pH 8 and adjusting the pH of the sample to pH 7.4 prior to the heat treatment step on the yield of antibody A. FIG. 5 also shows the effect of including a homogenization step or a cell slurry hold step. Numbers above each bar indicate the % increase in yield compared to the control with a step of homogenization but no step of pH adjustment.

FIG. 6 shows an SDS-PAGE analysis of antibody A samples extracted from cells after heat treatment.

Lane 1 is a molecular weight marker;

Lane 2 is a sample of antibody A;

Lane 3 is the sample after a homogenization step but no pH adjustment and no cell slurry hold;

Lane 4 is the sample after treatment with extraction buffer at pH 8 and adjustment to pH 7.4 prior to heat treatment and a homogenization step and no cell slurry hold;

Lane 5 is the sample after no pH adjustment, no homogenisation and no cell slurry hold;

Lane 6 is the sample after treatment with extraction buffer at pH 8 and adjustment to pH 7.4 prior to heat treatment and no homogenisation and no cell slurry hold;

Lane 7 is the sample after cell slurry hold but no pH adjustment and no homogenisation;

Lane 8 is the sample after treatment with extraction buffer at pH 8 and adjustment to pH 7.4 prior to heat treatment and a cell slurry hold but no homogenisation.

FIG. 7 is a graph showing the pH of the sample over time for a control sample having no pH adjustment, a sample having been treated with extraction buffer of pH 8, a sample having been treated with extraction buffer of pH 7.4 and a pH adjustment of the sample to pH 7.4 prior to the heat treatment step and a sample having been treated with extraction buffer of pH 8 and a pH adjustment of the sample to pH 7.4 prior to the heat treatment step. The first peak shows the point at which the extraction buffer was added and the second peak shows the point at which the pH of two of the samples was adjusted prior to the heat treatment step.

FIG. 8 is a histogram showing the effect of a control sample having no pH adjustment, a sample having been treated with extraction buffer of pH 7.4 and a pH adjustment of the sample to pH 7.4 prior to the heat treatment step, a sample having been treated with extraction buffer of pH 8, and a sample having been treated with extraction buffer of pH 8 and a pH adjustment of the sample to pH 7.4 prior to the heat treatment step on the yield of antibody A. Numbers above each bar indicate the % increase in yield compared to the control with no step of pH adjustment.

FIG. 9 is a histogram showing the effect of a control sample having no pH adjustment, a sample having been treated with extraction buffer of pH 7.4 and pH adjustment of the sample to 7.4 during the heat up phase prior to the heat treatment step, and a sample having been treated with extraction buffer of pH 8 and pH adjustment of the sample to 7.4 during the heat up phase prior to the heat treatment step on the yield of antibody A. Numbers above each bar indicate the % increase in yield compared to the control with no step of pH adjustment.

GENERAL METHOD

In the following examples, the method is performed as follows unless otherwise stated:
Cell Culture Step & Centrifugation:

Antibody A (a Fab') was expressed in *E. coli* W3110 cells using the vector pTT0D with DNA encoding antibody A inserted. Fermentation was performed at 25° C. for 30 hours after induction with lactose and ready for harvest. Fifty ml or 1 L harvest culture aliquots were centrifuged for 1 hour at 4200 RPM and at 4° C.

The supernatant was decanted and to simulate clarification at production scale a small proportion of the supernatant was added to the cells to bring the resulting cell slurry sample to 35% of the harvest weight.
Cell Slurry Hold Step (CSH):

In some experiments a cell slurry hold step was performed wherein the sample was held for 33 hours at 18° C. and 200 RPM prior to addition of the extraction buffer.
Addition of Extraction Buffer:

The resulting cell slurry sample (hereinafter referred to as the sample) was resuspended using a 300 mM Tris and 30 mM EDTA stock solution to a final concentration of 100 mM Tris and 10 mM EDTA having an adjusted pH of 7.4 using HCl. In experiments described below the pH of this extraction buffer is adjusted from the control pH of 7.4 to higher pH levels between pH 7.4 and 9.0.

Homogenisation Step (Homog.):

In some experiments a homogenisation step was performed after addition of the extraction buffer by a single passage at 1500 psi.
pH Adjustment Before Heat Up Phase:

In some experiments the sample was subjected to pH adjustment with 5 M NaOH to a desired level between 7.0 and 7.8 before the start of the heat up phase.
Heat Up Phase The samples were subjected to a heat up phase wherein the temperature of the sample was elevated from 18° C. up to the desired elevated temperature of 59° C. at which the heat treatment step started.
pH Adjustment During the Heat Up Phase:

In some experiments the sample was subjected to pH adjustment with 5 M NaOH to a desired level 7.4±0.02 during the heat up phase until the desired elevated temperature of 59° C. was reached.
Heat Treatment Step The sample was held at 59° C. for 10 to 12 hours and 200 RPM.

Post heat treatment, the resuspended cell pellets were clarified by centrifugation at 4200 rpm for 1 hour at 4° C. Supernatant containing functional antibody A was assayed for Fab' using Protein G HPLC analysis in 20 mM phosphate buffer. Antibody A was eluted using a pH gradient from pH 7.0 on injection, reducing to pH 2.5.

Reduced extract samples were run on Tris-Glycine SDS-PAGE gels with a load concentration of approximately 1 μg.

Example 1: Effect on pH of Sample after Addition of an Extraction Buffer

Figure 1:
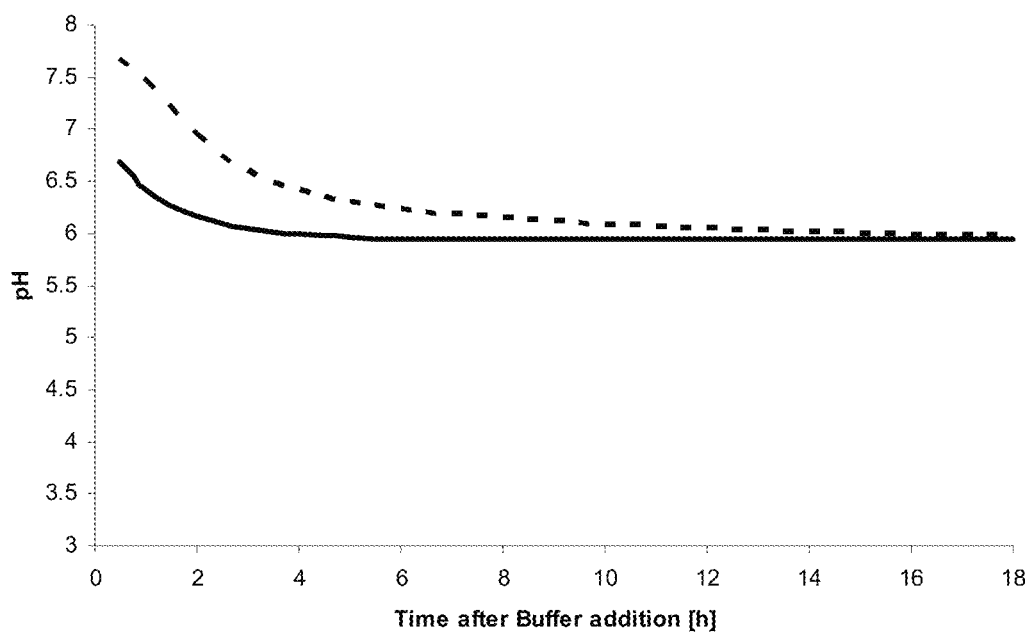

The cell culture step and addition of extraction buffer step, wherein the buffer had a pH of 8.0 or pH 7.4 were carried out as described in the General Method Section. The pH of the sample was monitored from addition of the extraction buffer. FIG. 1 shows that there is a rapid drop in the pH of the sample after addition of the buffer and the pH quickly drops below pH 7, especially when the buffer has a pH of 7.4.

Example 2: Effect of Extraction Buffer pH on Antibody Yield

The cell culture step, addition of extraction buffer step, heat up phase and heat treatment step were carried out as described in the General Methods Section.

The cell slurry hold step, the homogenisation step and the pH adjustment step before or during heat up were not carried out.

Figure 2A:
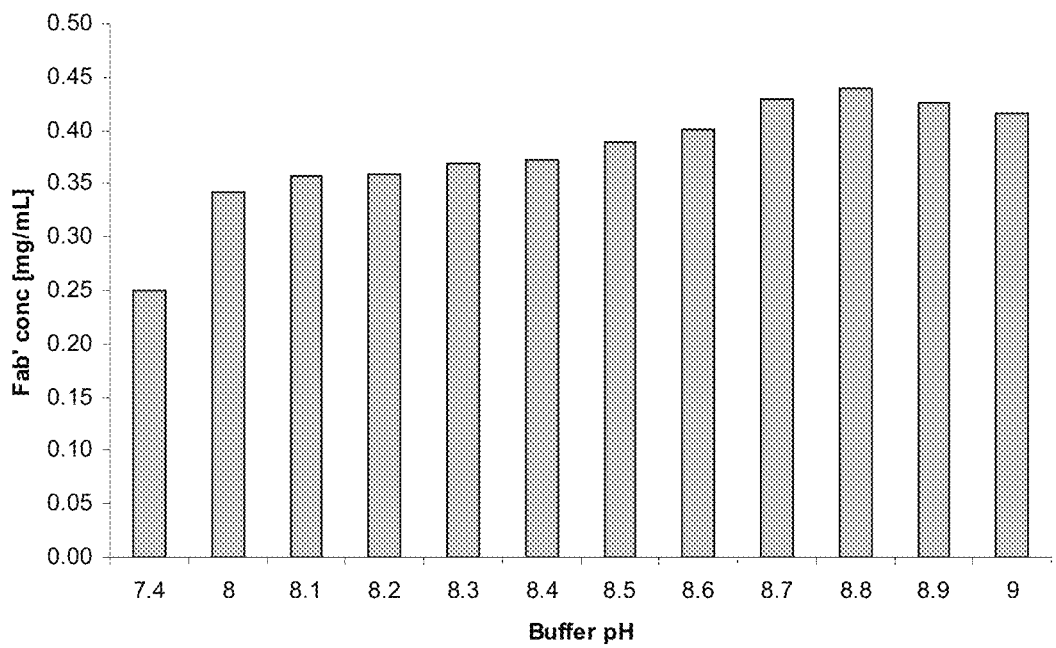

The pH of the extraction buffer was varied as follows: 7.4, 8.0. 8.1, 8.2, 8.3, 8.4, 8.5, 8.6, 8.7, 8.8, 8.9 and 9.0. The results are shown in FIG. 2a which shows the concentrations of Fab' after heat extraction. It can be seen that an elevated pH of the extraction buffer above 7.4 resulted in a significant increase on the recovery of Fab', increasing yield up to pH 8.8. Above 8.8 the concentrations of the Fab' started declining.

TABLE 1

| Extraction Buffer pH | pH of sample after centrifugation pre extraction buffer addition | pH of sample after Extraction buffer addition | pH of sample after 1 h hold pre heat up | pH of sample after heat treatment |
| --- | --- | --- | --- | --- |
| 7.4 | 5.25 | 6.36 | 5.67 | 5.54 |
| 8 | 5.25 | 7.62 | 6.35 | 5.8 |
| 8.1 | 5.26 | 7.74 | 6.53 | 5.85 |
| 8.2 | 5.26 | 7.87 | 6.96 | 5.96 |
| 8.3 | 5.26 | 7.98 | 7.4 | 6.17 |
| 8.4 | 5.27 | 8.07 | 7.62 | 6.44 |
| 8.5 | 5.26 | 8.16 | 7.84 | 6.9 |
| 8.6 | 5.28 | 8.23 | 7.98 | 7.23 |
| 8.7 | 5.27 | 8.3 | 8.12 | 7.59 |
| 8.8 | 5.26 | 8.37 | 8.19 | 7.73 |
| 8.9 | 5.27 | 8.42 | 8.31 | 8.03 |
| 9 | 5.28 | 8.51 | 8.41 | 8.17 |

Figure 2B:
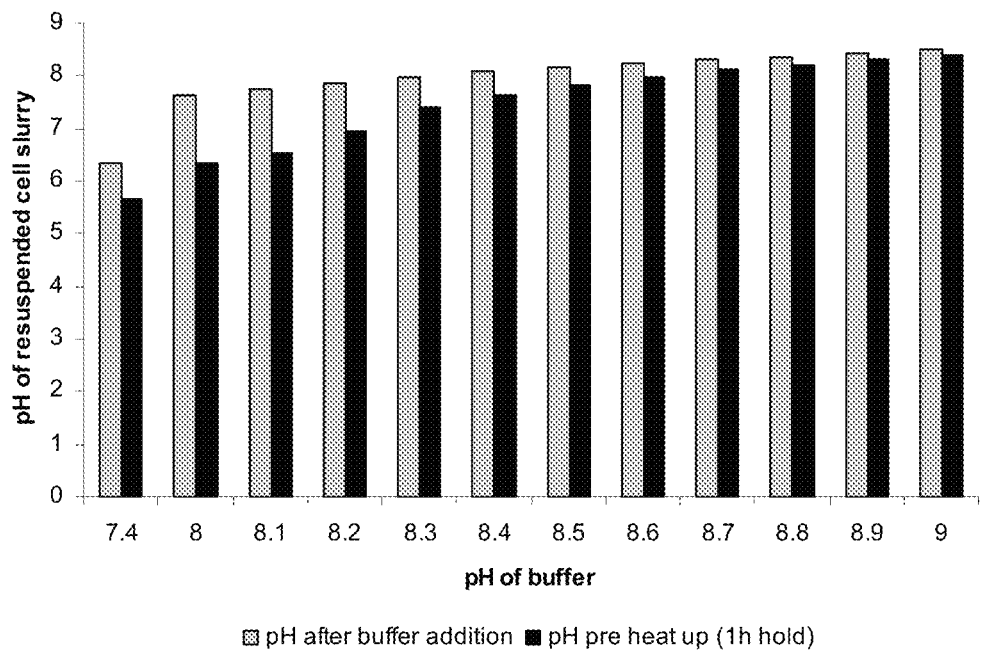

Table 1 and FIG. 2b show the pH of cell samples (resuspended cell slurry) directly after addition of the extraction buffer having a pH from 7.4 to 9.0 and the pH of the cell samples 1 hour after addition of the extraction buffer prior to the heat up phase.

Example 3: Effect of pH Prior to Heat Up Phase on Antibody Yield

The cell culture step, addition of extraction buffer step, homogenisation step, pH adjustment step before heat up, heat up phase and heat treatment step were carried out as described in the General Methods Section. The control was not subject to a pH adjustment step.

In the control experiment the extraction buffer was pH 7.4 and in the other experiments when the pH was adjusted prior to heat up phase, the extraction buffer was pH 8.0.

The cell slurry hold step and the pH adjustment step during heat up were not carried out.

In the control no pH adjustment prior to heat up phase was carried out. In the other experiments, the pH of the sample was adjusted prior to the heat up phase to pH 7.0, 7.2, 7.4, 7.6 and 7.8.

Figure 3A:
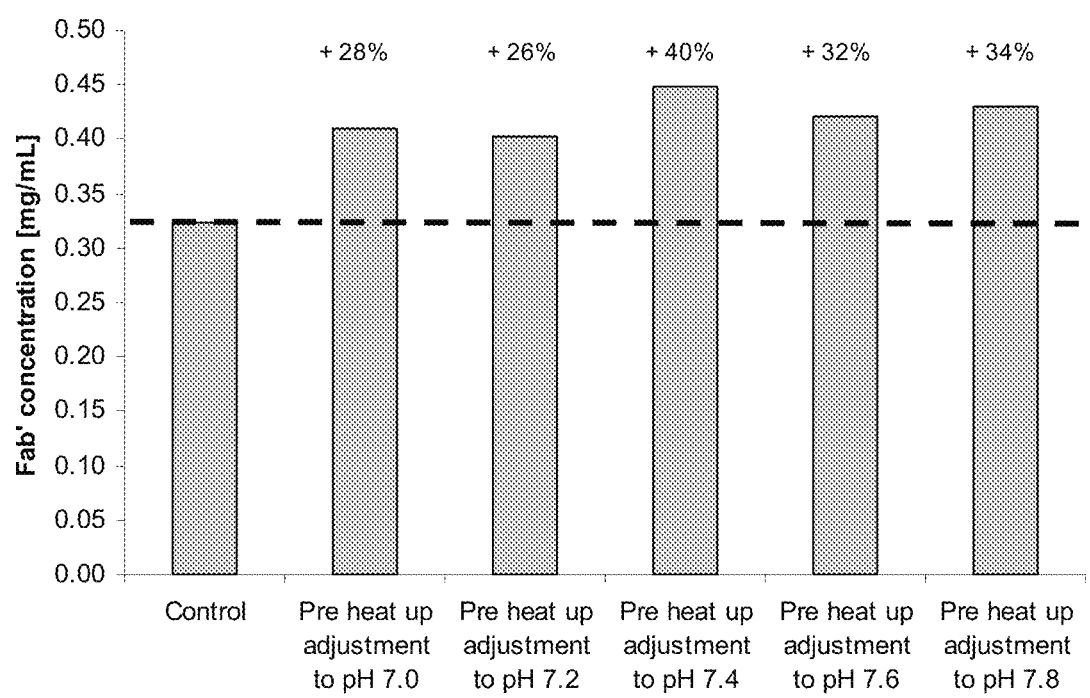

The results are shown in FIG. 3a which shows that this pH adjustment step resulted in improved Fab' recovery. FIG. 3a demonstrates how pH adjustment to set points within a range of pH 7.0 to 7.8 increased product recovery by 26 to 40% compared to the control sample which was not subjected to pH adjustment.

Figure 3B:
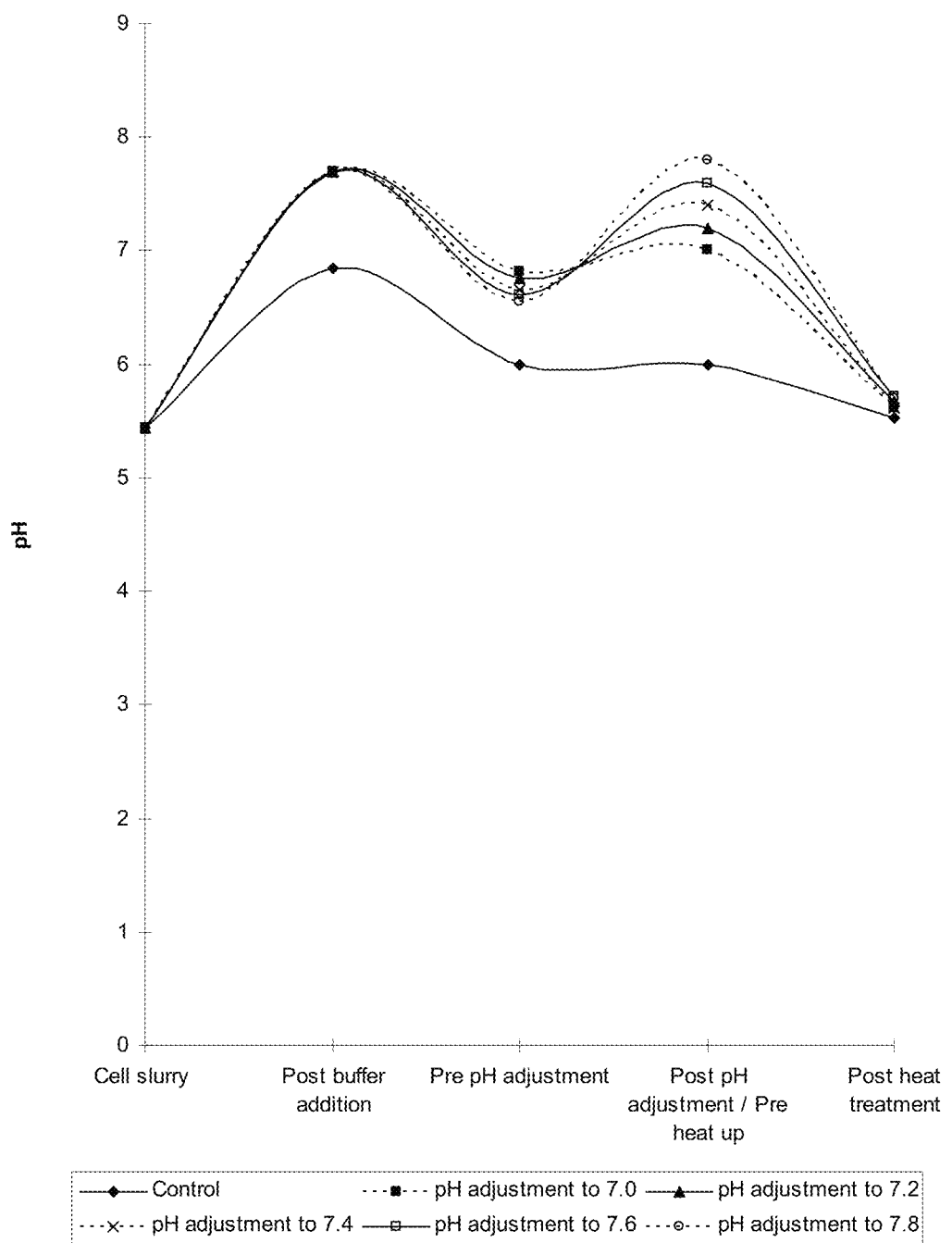

The pH of the sample was detected at various points in the method. Table 2 above and FIG. 3b show the varying pH of the samples through the various stages of the method: the cell slurry (after culturing and centrifugation); post buffer addition (directly after addition of the extraction buffer); pre pH adjustment; post pH adjustment but pre heat up phase; and post heat treatment step.

Figure 4:
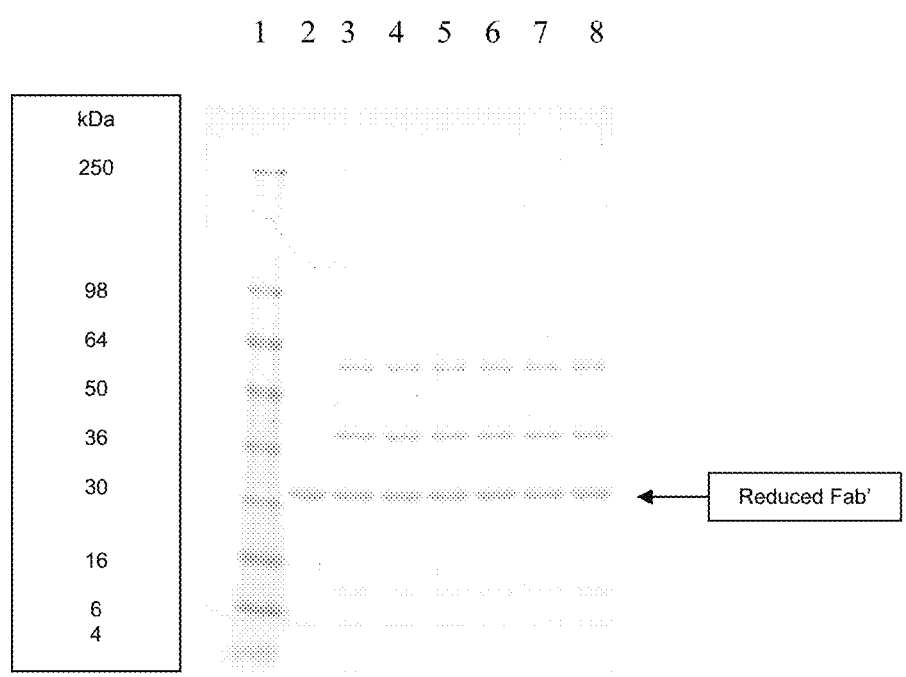

The SDS-PAGE gel in FIG. 4 shows the protein profiles of post extraction samples.

Lane 1 is a molecular weight marker, Lane 2 is a sample of antibody A, Lane 3 is the sample after no pH adjustment and Lanes 4 to 8 show samples after pH adjustment to 7.0, 7.2, 7.4, 7.6 and 7.8 respectively prior to the heat treatment step.

The sample load weight was normalized to 1 μg Fab'. No significant differences in protein profiles were observed between control and samples with pre heat up pH adjustment.

Example 4: Effect of Extraction Buffer pH and pH Adjustment on Antibody Yield in the Presence and Absence of a Cell Slurry Hold Step and Homogenisation Step The following experiments were carried out as described in the General Methods Section.

Control (with homog.): cell culture step, addition of extraction buffer step (pH 7.4), homogenisation step, heat up phase and heat treatment step;

Buffer at pH 8 and pre heat up adjustment to pH 7.4 (with homog.): cell culture step, addition of extraction buffer step (pH 8), homogenisation step, pH adjustment step before heat up to pH 7.4, heat up phase, and heat treatment step;

TABLE 2

| | Process Step | | | | |
| --- | --- | --- | --- | --- | --- |
| Sample | 1 Cell slurry pH | 2 Post buffer addition PH | 3 Pre pH adjustment PH | 4 Post pH adjustment/Pre heat up pH | 5 Post heat treatment pH |
| Control | 5.44 | 6.84 | 5.99 | 5.99 | 5.52 |
| pH adjustment to 7.0 | 5.44 | 7.7 | 6.82 | 7 | 5.61 |
| pH adjustment to 7.2 | 5.44 | 7.7 | 6.75 | 7.2 | 5.67 |
| pH adjustment to 7.4 | 5.44 | 7.7 | 6.65 | 7.4 | 5.62 |
| pH adjustment to 7.6 | 5.44 | 7.7 | 6.61 | 7.6 | 5.71 |
| pH adjustment to 7.8 | 5.44 | 7.7 | 6.55 | 7.8 | 5.7 |

Control (without homog. or CSH): cell culture step, addition of extraction buffer step (pH 7.4), heat up phase and heat treatment step;

Buffer at pH 8 and pre heat up adjustment to pH 7.4 (without homog. or CSH): cell culture step, addition of extraction buffer step (pH 8), pH adjustment step before heat up to pH 7.4, heat up phase, and heat treatment step;

Control (with CSH): cell culture step, cell slurry hold step, addition of extraction buffer step (pH 7.4), heat up phase and heat treatment step; and Buffer at pH 8 and pre heat up adjustment to pH 7.4 (with CSH): cell culture step, cell slurry hold step, addition of extraction buffer step (pH 8), pH adjustment step before heat up to pH 7.4, heat up phase, and heat treatment step.

Figure 5:
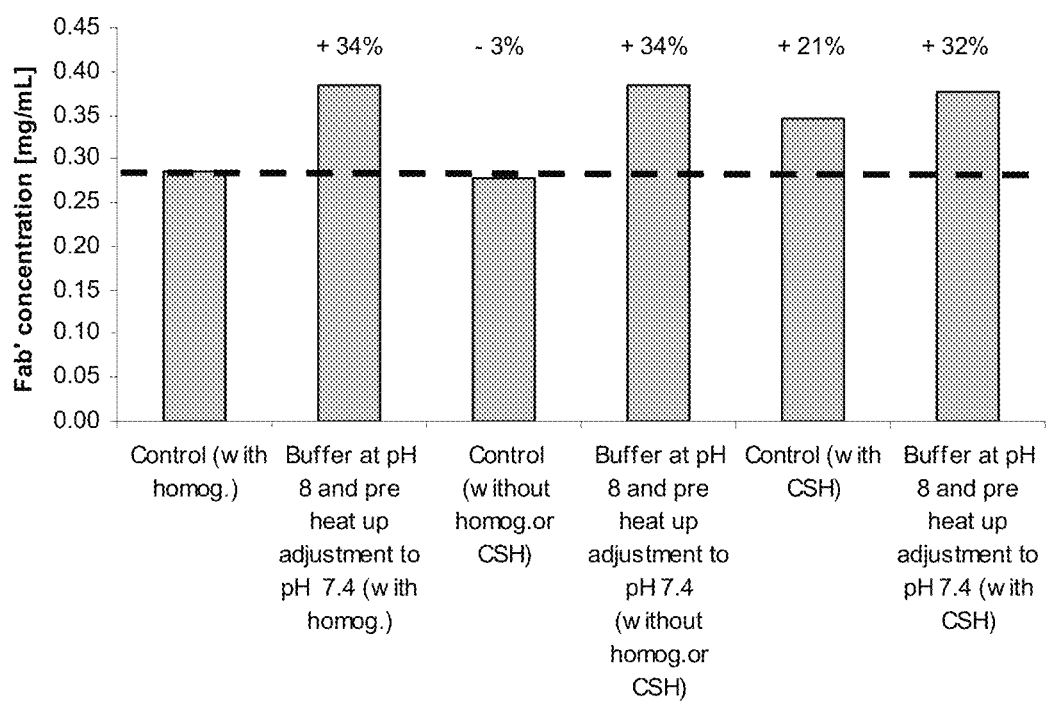

FIG. 5 shows the results of the above experiments. It can be seen that the addition of the pH adjustment step prior to heat up resulted in ~34% higher extraction titers in comparison to the control. It can also be seen that inclusion of the homogenization step had no effect on yield when compared with method with the pH adjustment step. Cell slurry hold gives increased yield when comparing control extractions, but not when comparing those with pH adjustment step.

Figure 6:
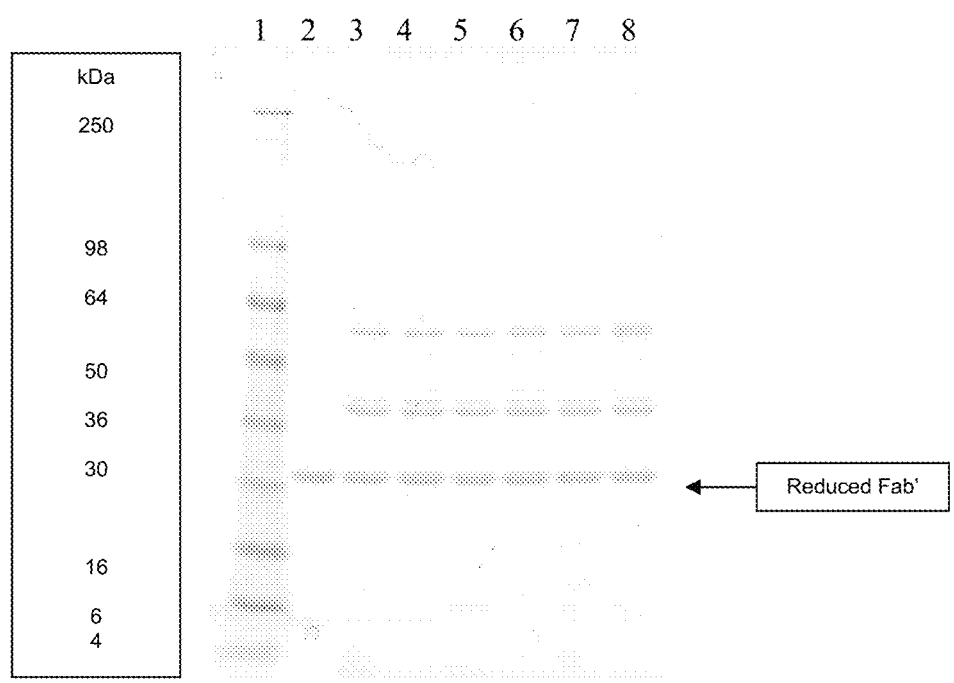

The SDS-PAGE gel in FIG. 6 shows the protein profiles of post extraction samples.

Lane 1 is a molecular weight marker;

Lane 2 is a sample of antibody A;

Lane 3 is the sample after a homogenization step but no pH adjustment and no cell slurry hold;

Lane 4 is the sample after treatment with extraction buffer at pH 8 and adjustment to pH 7.4 prior to heat treatment and a homogenization step and no cell slurry hold;

Lane 5 is the sample after no pH adjustment, no homogenisation and no cell slurry hold;

Lane 6 is the sample after treatment with extraction buffer at pH 8 and adjustment to pH 7.4 prior to heat treatment and no homogenisation and no cell slurry hold;

Lane 7 is the sample after cell slurry hold but no pH adjustment and no homogenisation;

Lane 8 is the sample after treatment with extraction buffer at pH 8 and adjustment to pH 7.4 prior to heat treatment and a cell slurry hold but no homogenisation.

The protein profiles of extracts with pH adjustment were comparable to cell slurry hold controls.

Example 5: Effect of pH of Extraction Buffer and/or pH Adjustment Step Before Heat Up on pH of Sample and Fab' Yield The cell culture step, addition of extraction buffer step, heat up phase and heat treatment step were carried out as described in the General Methods Section. Two experiments included a pH adjustment before heat up step and two did not include this step.

The cell slurry hold step, the homogenisation step and the pH adjustment step during heat up were not carried out.

Four different pH control strategies were carried out:
1. Control: extraction buffer pH 7.4 and no pH adjustment before heat up;
2. Extraction buffer pH 7.4 and pH adjustment to 7.4 prior to heat up;
3. Buffer pH 8: Extraction buffer pH 8.0 and no pH adjustment prior to heat up; and
4. Extraction buffer pH 8.0 and pH adjustment to 7.4 prior to heat up.

Figure 7:
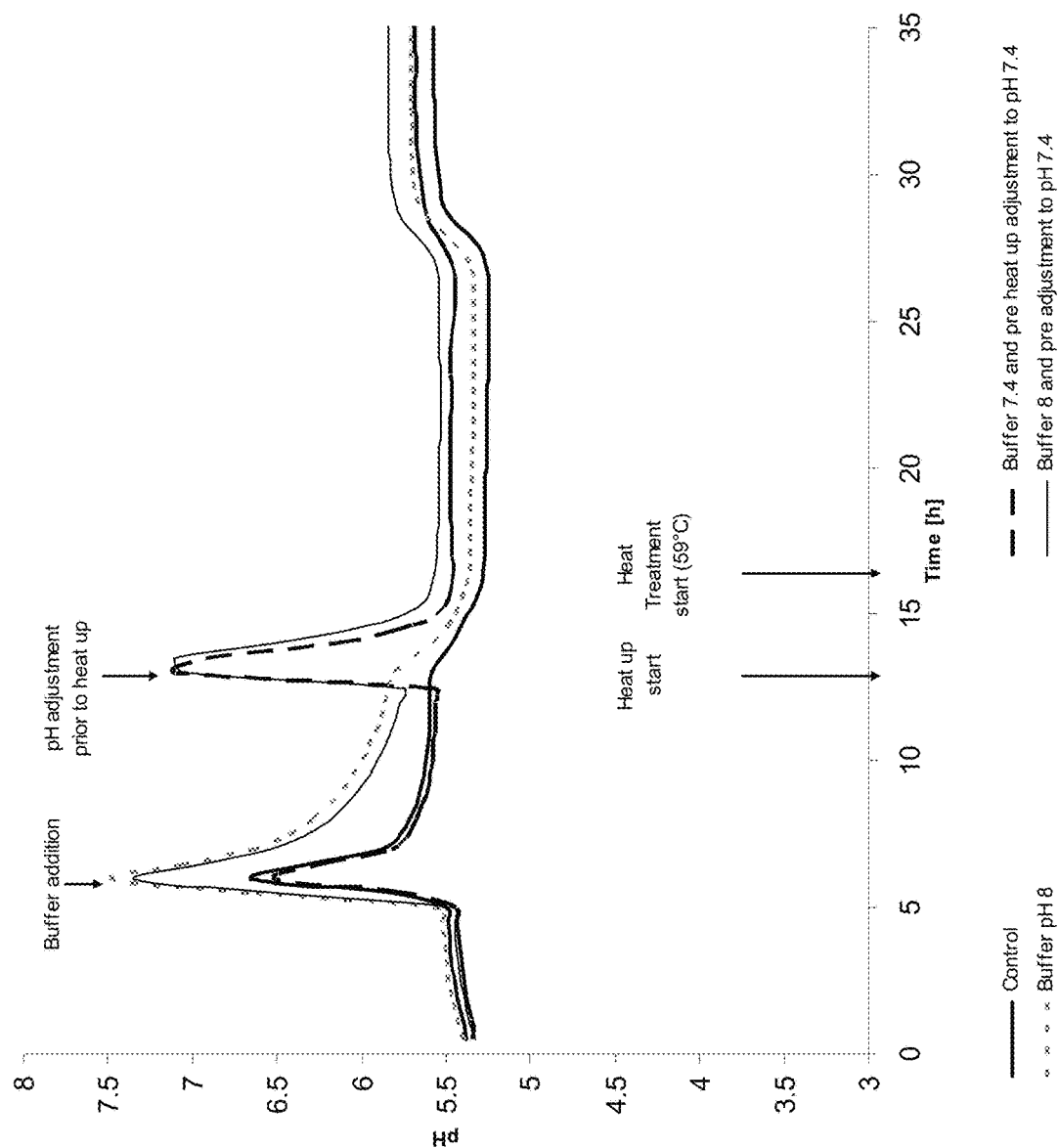

The pH was monitored throughout the primary recovery starting from cell slurry over buffer addition (first peak), pH adjustment prior to heat up (second peak) and heat treatment (pH drop). FIG. 7 shows the pH profile during the methods.

Figure 8:
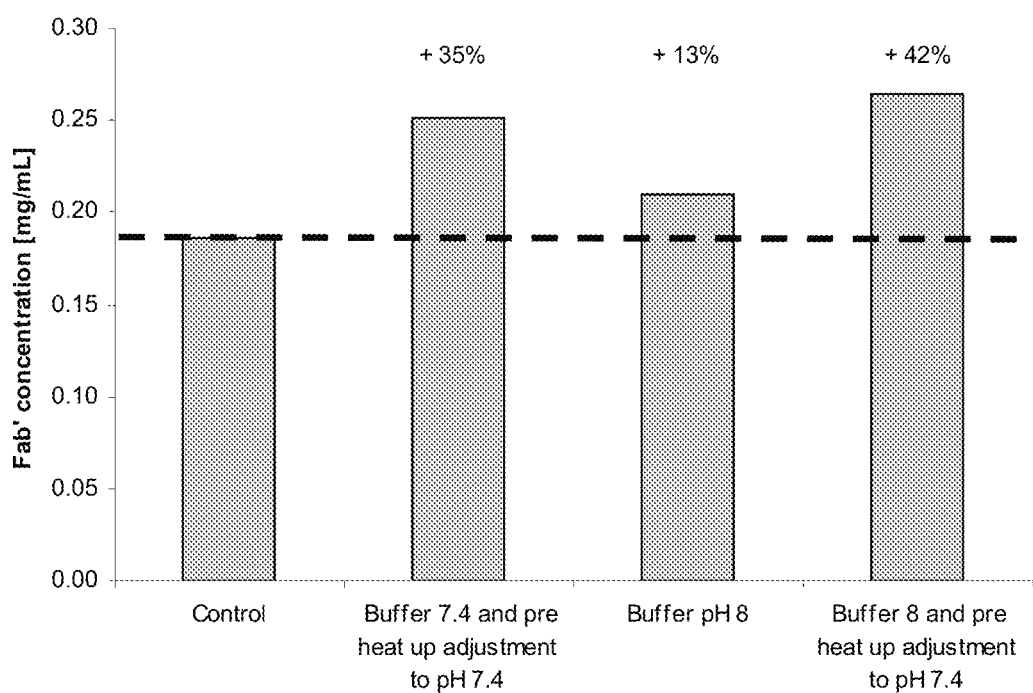

The effect on Fab' yield is shown in FIG. 8, were it can be seen that all pH elevation strategies (1 to 3) resulted in Fab' yield increase and strategy 4 using a combination of elevated buffer and pre heat up pH adjustment resulted in the highest Fab' recoveries.

Example 6: Effect of pH of Extraction Buffer and/or pH Adjustment Step During Heat Up on pH of Sample and Fab' Yield The cell culture step, addition of extraction buffer step, heat up phase and heat treatment step were carried out as described in the General Methods Section. Two experiments included a pH adjustment during heat up step and the control did not include this step.

The cell slurry hold step, the homogenisation step and the pH adjustment step before heat up were not carried out.

Three different pH control strategies were carried out:
1. Control: extraction buffer pH 7.4 and no pH adjustment during heat up;
2. Extraction buffer pH 7.4 and pH adjustment to 7.4 during heat up;
3. Extraction buffer pH 8.0 and pH adjustment to 7.4 during heat up.

Figure 9:
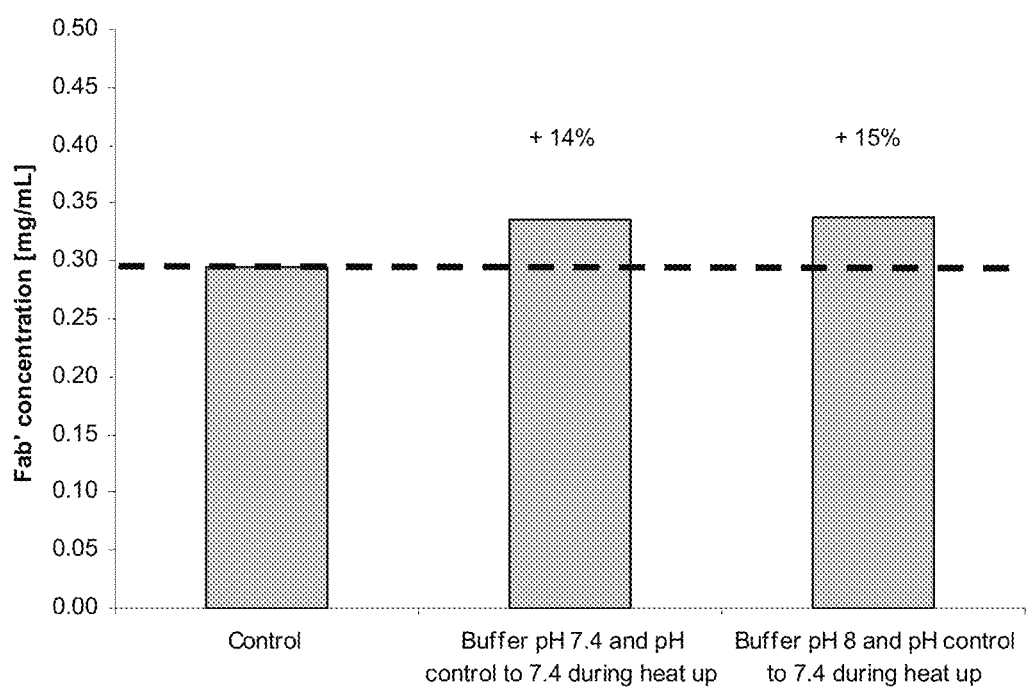
Figure 10:
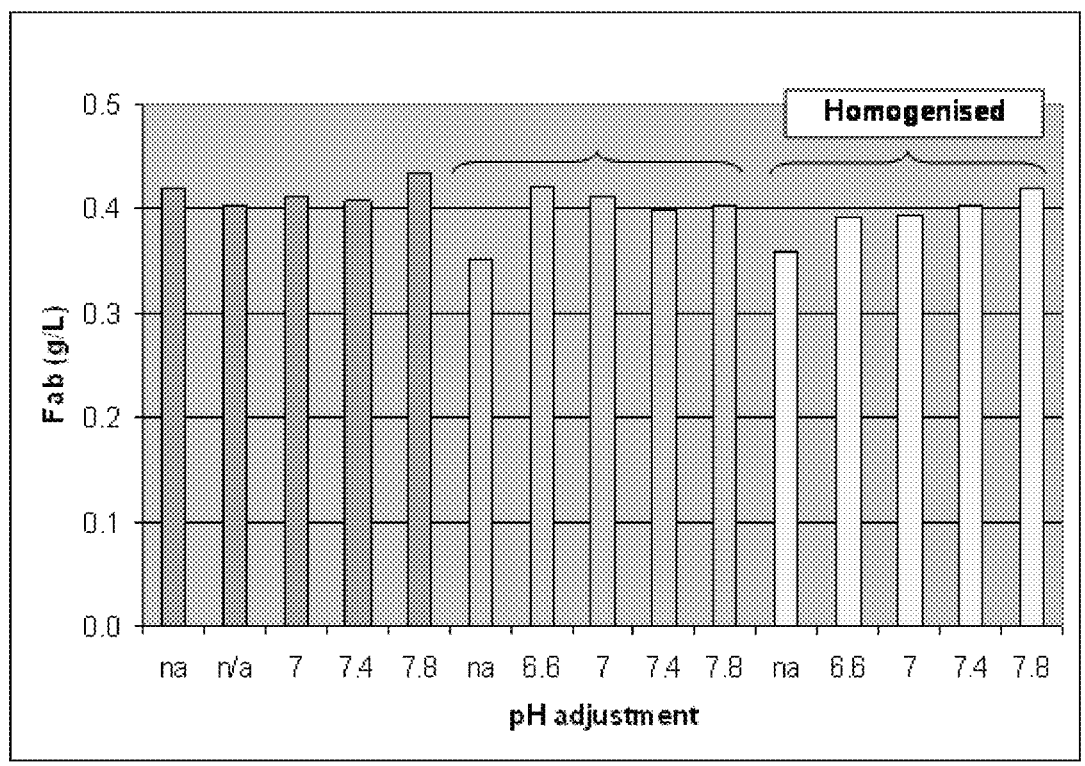
FIG. 10 is a histogram showing the effect of pH adjustment to 6.6, 7.0, 7.4 and 7.8 units on the Fab' titre compared to a non-pH adjusted control. The experiment is repeated with three different pre-treatment steps (prior to extraction) of no pre-treatment, cell slurry hold and homogenisation.
Figure 11:
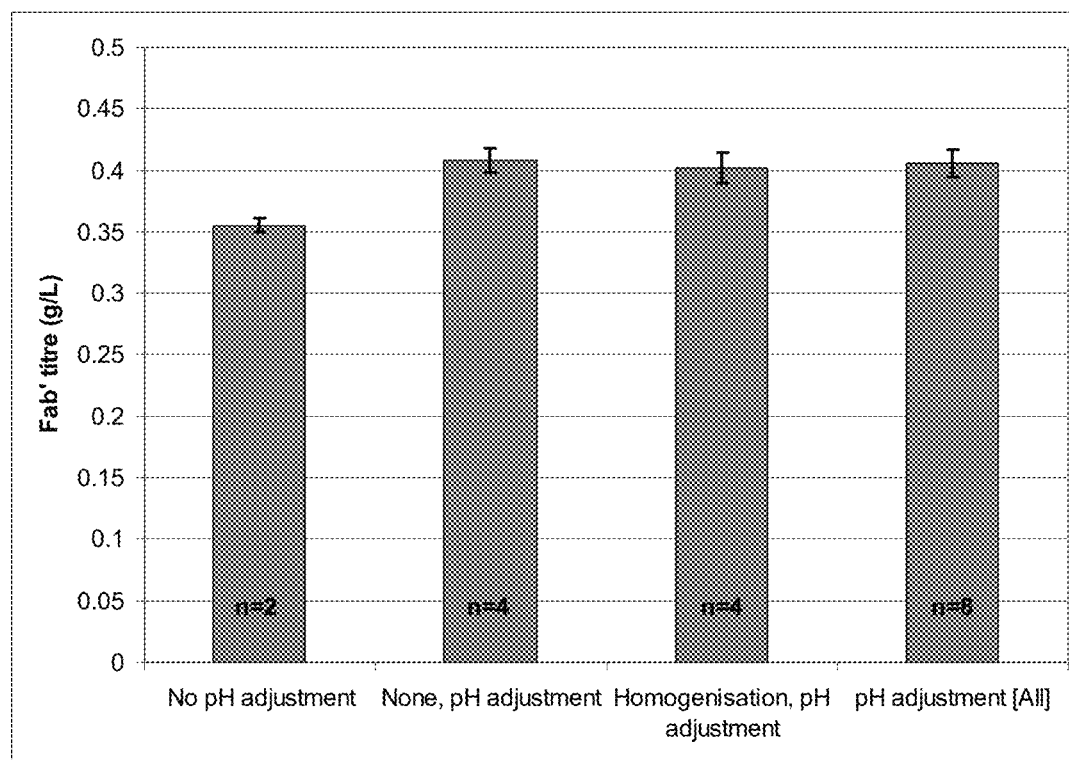
FIG. 11 is a histogram showing the average Fab' titre of the following conditions; no pH adjustment, no pre-treatment and pH adjustment (to the range 6.6-7.8 units), homogenisation and pH adjustment (to the range 6.6-7.8 units) and all pH adjusted conditions (homogenisation and no pre-treatment). Error bars show one standard deviation from the mean.

The effect on Fab' yield is shown in FIG. 9, where it can be seen that all pH elevation strategies (2 and 3) resulted in Fab' yield increase and strategy 4 using a combination of elevated buffer and pH adjustment during heat up resulted in the highest Fab' recoveries.

Example 7

The experiment was carried out by taking fermentation broth and centrifuging to remove the majority of the spent medium thus producing a cell slurry. This cell slurry was held in the case of the cell slurry hold for 33 hours. In the case of the homogenized and no pre-treatment conditions the cells were resuspended in extraction buffer and either homogenized or were heat extracted without any pre-treatment. Following the cell slurry hold the cells were resuspended in extraction buffer. Once all conditions were resuspended in extraction buffer they were pH adjusted to the desired setpoint (shown in FIG. 12) and the heat extraction (59° C. for 10 hours) was initiated. Following heat extraction the extract was clarified by centrifugation in order to determine the Fab' titre in the liquid phase.

The data below is also represented in FIG. 12.

| pretreatment | pH adjustment | Post extraction (g/L) | on no pretreatment, no ph adjust Increase over control (%) |
| --- | --- | --- | --- |
| CSH | na | 0.419 | 19.27 |
| CSH | n/a | 0.402 | 14.52 |
| CSH | 7 | 0.412 | 17.40 |
| CSH | 7.4 | 0.408 | 16.29 |
| CSH | 7.8 | 0.435 | 23.86 |
| None | na | 0.351 | 0.00 |
| None | 6.6 | 0.421 | 19.89 |
| None | 7 | 0.412 | 17.40 |
| None | 7.4 | 0.399 | 13.63 |
| None | 7.8 | 0.403 | 14.72 |
| Homogenisation | na | 0.359 | 2.29 |
| Homogenisation | 6.6 | 0.392 | 11.79 |

-continued

| pretreatment | pH adjustment | Post extraction (g/L) | on no pretreatment, no ph adjust Increase over control (%) |
|---|---|---|---|
| Homogenisation | 7 | 0.394 | 12.16 |
| Homogenisation | 7.4 | 0.403 | 14.80 |
| Homogenisation | 7.8 | 0.420 | 19.60 |

Control was no pre-treatment and no pH control.

We claim:

1. A composition comprising a recombinant antibody and an extraction buffer, said composition being obtained from a method comprising culturing a host cell sample transformed with an expression vector encoding a recombinant antibody molecule; separating the host cell sample from medium in which the host cell was cultured; adding an extraction buffer to the separated host cell sample; detecting the pH of the extraction buffer containing the separated host sample after the extraction buffer is added and adjusting the pH of the extraction buffer containing the separated host sample to a pH of 6-9; and subjecting the sample to a heat treatment step, wherein:
   a) the recombinant antibody is a VH, VL, VHH, Fab, modified Fab, altered hinge Fab, Fab', F(ab')$_2$, Fv fragment; a light chain or heavy chain monomer or dimer; a single chain antibody or a dual specificity antibody; and
   b) the recombinant antibody is produced in bacterial cells, yeast cells, Chinese Hamster Ovary (CHO) cells, myeloma cell lines, or hybridoma cell lines.

2. The composition according to claim 1, wherein said heat treatment step is performed within the range of 30° C. to 70° C.

3. The composition according to claim 1, wherein the antibody specifically binds to an antigen selected from TNF-α, VLA-4, E-selectin, P selectin, L-selectin, CD2, CD3, CD4, CD5, CD7, CD8, CD11a, CD11b, CD18, CD19, CD20, CD23, CD25, CD33, CD38, CD40, CD40L, CD45, CDW52, CD69, CD134 (OX40), ICOS, BCMP7, CD137, CD27L, CDCP1, CSF1, CSF1-Receptor, DPCR1, DPCR1, dudulin2, FLJ20584, FLJ40787, HEK2, KIAA0634, KIAA0659, KIAA1246, KIAA1455, LTBP2, LTK, MAL2, MRP2, nectin-like2, NKCC1, PTK7, RAIG1, TCAM1, SC6, BCMP101, BCMP84, BCMP11, DTD, carcinoembryonic antigen (CEA), human milk fat globulin (HMFG1 and 2), MHC Class I antigens, MHC Class II antigens, KDR or VEGF.

4. The composition according to claim 1, wherein the antibody molecule is selected from a VH, VL, VHH, Fab, modified Fab, altered hinge Fab, Fab', F(ab')$_2$, Fv fragment; a light chain or heavy chain monomer or dimer; a single chain antibody or a dual specificity antibody.

5. The composition according to claim 1, wherein the pH is adjusted, to ensure that the pH of the sample is 6 to 9 prior to the heat treatment step.

6. The composition according to claim 1, wherein said antibody binds to TNF-α.

7. The composition according to claim 6, wherein the antibody is selected from a VH, VL, VHH, Fab, modified Fab, altered hinge Fab, Fab', F(ab')$_2$, Fv fragment; a light chain or heavy chain monomer or dimer; a single chain antibody or a dual specificity antibody.

8. The composition according to claim 7, wherein said antibody is a Fab'.

9. The composition according to claim 2, wherein said heat treatment step is performed within the range of 40° C. to 65° C.

10. The composition according to claim 2, wherein said heat treatment step is performed within the range of 45° C. to 60° C.

11. The composition according to claim 1, wherein said heat treatment step is performed for a period of between 6 and 16 hours.

12. The composition according to claim 1, wherein said heat treatment step is performed for a period of between 4 and 18 hours.

13. The composition according to claim 1, wherein the extraction buffer is a Tris(hydroxymethyl)aminomethane/Ethylenedinitrilotetraacetic acid disodium salt dehydrate (Tris/EDTA) buffer.

* * * * *